United States Patent
Narayanan et al.

(10) Patent No.: US 9,574,085 B2
(45) Date of Patent: *Feb. 21, 2017

(54) BIOCOMPATIBLE N, N-DISUBSTITUTED SULFONAMIDE-CONTAINING FLUORESCENT DYE LABELS

(75) Inventors: Narasimhachari Narayanan, Westford, MA (US); Kevin Groves, Somerville, MA (US); Jeffrey D. Peterson, Shrewsbury, MA (US); Milind Rajopadhye, Westford, MA (US)

(73) Assignee: VisEn Medical, Inc., Waltham, MA (US)

( * ) Notice: Subject to any disclaimer, the term of this patent is extended or adjusted under 35 U.S.C. 154(b) by 563 days.

This patent is subject to a terminal disclaimer.

(21) Appl. No.: 12/065,387

(22) PCT Filed: Sep. 1, 2006

(86) PCT No.: PCT/US2006/034260
§ 371 (c)(1),
(2), (4) Date: Dec. 18, 2008

(87) PCT Pub. No.: WO2007/028037
PCT Pub. Date: Mar. 8, 2007

(65) Prior Publication Data
US 2009/0130024 A1    May 21, 2009

Related U.S. Application Data

(60) Provisional application No. 60/713,632, filed on Sep. 2, 2005.

(51) Int. Cl.
*A61K 49/00* (2006.01)
*C07D 401/14* (2006.01)
*C07D 403/06* (2006.01)
*C07D 403/12* (2006.01)
*C07D 403/14* (2006.01)
*C09B 23/08* (2006.01)
*C07D 209/14* (2006.01)
*C09B 23/01* (2006.01)
*G01N 33/533* (2006.01)
*G01N 33/537* (2006.01)
*G01N 33/58* (2006.01)

(52) U.S. Cl.
CPC ......... *C09B 23/086* (2013.01); *A61K 49/0032* (2013.01); *A61K 49/0052* (2013.01); *C07D 209/14* (2013.01); *C07D 401/14* (2013.01); *C07D 403/06* (2013.01); *C07D 403/14* (2013.01); *C09B 23/0066* (2013.01); *C09B 23/083* (2013.01); *G01N 33/533* (2013.01); *G01N 33/537* (2013.01); *G01N 33/582* (2013.01)

(58) Field of Classification Search
None
See application file for complete search history.

(56) References Cited

U.S. PATENT DOCUMENTS

| | | |
|---|---|---|
| 3,782,933 A | 1/1974 | Ohlschlager et al. |
| 4,264,694 A | 4/1981 | Pu et al. |
| 4,370,401 A | 1/1983 | Winslow et al. |
| 4,981,977 A | 1/1991 | Southwick et al. |
| 5,073,171 A | 12/1991 | Eaton |
| 5,268,486 A | 12/1993 | Waggoner et al. |
| 5,486,616 A | 1/1996 | Waggoner et al. |
| 5,491,151 A | 2/1996 | Nakagawa et al. |
| 5,569,587 A | 10/1996 | Waggoner |
| 5,569,766 A | 10/1996 | Waggoner et al. |
| 5,593,658 A | 1/1997 | Bogdanov et al. |
| 5,605,809 A | 2/1997 | Komoriya et al. |
| 5,627,027 A | 5/1997 | Waggoner |
| 5,808,044 A | 9/1998 | Brush et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,027,709 A | 2/2000 | Little et al. |
| 6,043,025 A | 3/2000 | Minden et al. |
| 6,083,485 A | 7/2000 | Licha et al. |
| 6,083,486 A | 7/2000 | Weissleder et al. |
| 6,127,134 A | 10/2000 | Minden et al. |
| 6,130,094 A | 10/2000 | Waggoner et al. |
| 6,133,445 A | 10/2000 | Waggoner et al. |
| 6,136,612 A | 10/2000 | Della Ciana et al. |

(Continued)

FOREIGN PATENT DOCUMENTS

| | | | |
|---|---|---|---|
| EP | 0417941 B1 | 3/1991 | |
| EP | 0820057 B1 | 1/1998 | |
| EP | 1065250 | * 1/2001 | ............ C09B 23/02 |
| EP | 1090961 A1 | 4/2001 | |
| EP | 1219626 B1 | 7/2002 | |
| EP | 1065250 B1 | 12/2004 | |
| JP | 10071766 A | 3/1998 | |
| WO | WO-9740104 A1 | 10/1997 | |
| WO | WO-9931181 A1 | 6/1999 | |
| WO | WO-9951702 A1 | 10/1999 | |
| WO | WO-0016810 A1 | 3/2000 | |
| WO | WO00/64988 | 11/2000 | |
| WO | WO-0121624 A1 | 3/2001 | |
| WO | WO-2007/028163 A1 | 3/2007 | |
| WO | WO-2009114776 A2 | 9/2009 | |

OTHER PUBLICATIONS

Dorwald F. A. Side Reactions in Organic Synthesis, 2005, Wiley: VCH, Weinheim. relevant portions attached.*

(Continued)

*Primary Examiner* — Alicia L Otton
(74) *Attorney, Agent, or Firm* — Goodwin Procter LLP

(57) ABSTRACT

This invention relates to new fluorescent chemical entities, especially fluorescent molecules that comprise biocompatible N,N-disubstituted sulfonamide fluorochromes. This invention also relates to the corresponding reactive versions of such molecules. This invention also relates to the corresponding conjugates with moieties such as peptides, proteins, various biomolecules, carbocyclic and heterocyclic compounds, sugars, and their uses thereof.

15 Claims, 3 Drawing Sheets

(56) References Cited

U.S. PATENT DOCUMENTS

| | | | |
|---|---|---|---|
| 6,248,904 B1 | 6/2001 | Zhang et al. | |
| 6,258,340 B1 | 7/2001 | Licha et al. | |
| 6,448,008 B1 * | 9/2002 | Caputo et al. | 435/6 |
| 6,534,041 B1 | 3/2003 | Licha et al. | |
| 6,592,847 B1 | 7/2003 | Weissleder et al. | |
| 6,620,858 B2 | 9/2003 | Cyr et al. | |
| 6,740,755 B2 | 5/2004 | Caputo et al. | |
| 6,747,159 B2 | 6/2004 | Caputo et al. | |
| 6,869,593 B2 | 3/2005 | Frangioni | |
| 6,913,743 B2 | 7/2005 | Licha et al. | |
| 6,926,885 B2 | 8/2005 | Licha et al. | |
| 6,995,262 B1 | 2/2006 | Deroover et al. | |
| 7,025,949 B2 | 4/2006 | Licha et al. | |
| 7,374,746 B2 | 5/2008 | Frangioni | |
| 7,445,767 B2 | 11/2008 | Licha et al. | |
| 7,488,468 B1 | 2/2009 | Miwa et al. | |
| 7,647,091 B2 | 1/2010 | Ntziachristos et al. | |
| 7,655,217 B2 | 2/2010 | Licha et al. | |
| 7,947,256 B2 | 5/2011 | Rajopadhye et al. | |
| 8,173,819 B2 | 5/2012 | Rajopadhye et al. | |
| 8,221,721 B2 | 7/2012 | Narayanan | |
| 8,420,055 B2 | 4/2013 | Gaw et al. | |
| 8,455,651 B2 | 6/2013 | Rajopadhye et al. | |
| 8,486,373 B2 | 7/2013 | Weissleder et al. | |
| 8,685,370 B2 | 4/2014 | Rajopadhye et al. | |
| 8,771,646 B2 | 7/2014 | Rajopadhye et al. | |
| 8,815,214 B2 | 8/2014 | Rajopadhye et al. | |
| 8,864,821 B2 | 10/2014 | Jaffer et al. | |
| 2003/0044353 A1 | 3/2003 | Weissleder et al. | |
| 2003/0124194 A1 | 7/2003 | Gaw et al. | |
| 2005/0106106 A1 | 5/2005 | Licha et al. | |
| 2005/0169843 A1 | 8/2005 | Weissleder et al. | |
| 2005/0169844 A1 | 8/2005 | Licha et al. | |
| 2005/0171434 A1 | 8/2005 | Madden et al. | |
| 2006/0099712 A1 | 5/2006 | Gilman et al. | |
| 2006/0275775 A1 | 12/2006 | Weissleder et al. | |
| 2008/0102036 A1 | 5/2008 | Poss et al. | |
| 2008/0226562 A1 | 9/2008 | Groves et al. | |
| 2008/0267883 A1 | 10/2008 | Rajopadhye et al. | |
| 2008/0286207 A1 | 11/2008 | Narayanan | |
| 2008/0312540 A1 | 12/2008 | Ntziachristos | |
| 2008/0317676 A1 | 12/2008 | Rajopadhye et al. | |
| 2009/0068115 A1 | 3/2009 | Gaw et al. | |
| 2009/0123383 A1 | 5/2009 | Frangioni | |
| 2009/0130024 A1 | 5/2009 | Narayanan et al. | |
| 2009/0220430 A1 | 9/2009 | Rajopadhye et al. | |
| 2010/0074847 A1 | 3/2010 | Madden et al. | |
| 2010/0078576 A1 | 4/2010 | Ntziachristos et al. | |
| 2010/0129293 A1 | 5/2010 | Licha et al. | |
| 2010/0166659 A1 | 7/2010 | Licha et al. | |
| 2010/0172841 A1 | 7/2010 | Peterson et al. | |
| 2010/0189657 A1 | 7/2010 | Weissleder et al. | |
| 2010/0268070 A1 | 10/2010 | Jaffer et al. | |
| 2011/0152501 A1 | 6/2011 | Weissleder et al. | |
| 2011/0165075 A1 | 7/2011 | Rajopadhye et al. | |
| 2011/0171136 A1 | 7/2011 | Poss et al. | |
| 2011/0256065 A1 | 10/2011 | Frangioni | |
| 2012/0321563 A1 | 12/2012 | Groves et al. | |
| 2013/0137873 A1 | 5/2013 | Narayanan | |
| 2014/0050662 A1 | 2/2014 | Ho | |
| 2014/0314677 A1 | 10/2014 | Groves et al. | |
| 2014/0348746 A1 | 11/2014 | Narayanan | |
| 2015/0018517 A1 | 1/2015 | Rajopadhye et al. | |
| 2015/0133773 A1 | 5/2015 | Jaffer et al. | |

OTHER PUBLICATIONS

Ernst et al. (1989) "Cyanine Dye Labelling Reagents for Sulphydryl Groups", *Cytometry*, 10:3-10.

Ficken, (1971) "The Chemistry of Synthetic Dyes", vol. 4, K. Venkataraman Ed., Academic Press, New York, p. 211-223.

Fry (1977) "Rodd's Chemistry of Carbon Compounds", "Cyanine Dyes and Related Compounds", Elsevier, Amsterdam. vol. IVb, Chapter 15, p. 369-424.

International Search Report and Written Opinion for International Patent Application No. PCT/US2006/034260, dated Jan. 31, 2007, 9 pages.

Lindsey et al. (1989) Visible Light Harvesting in Covalently-Linked Porphyrin Cyanine Dyes, *Tetrahedron*, 45:4845-4866.

Montet et al. (2006) "An Albumin-Activated Far-Red Fluorochrome for In Vivo Imaging " *Chem. Med. Chem.* 1(1):66-69.

Mujumdar et al. (1989) "Cyanine Dye Labelling Reagents Containing Isothiocyanate Groups", *Cytometry*, 10:11-19.

Mujumdar et al. (1993) "Cyanine Dye Labelling Reagents: Sulfoindocyanine Succinimidyl Esters", *Bioconjugate Chemistry*, 4:105-111.

Mujumdar et al. (1996) "Cyanine Labelling Reagents: Sulfobenzoindocyanine Succinimidyl Esters", *Bioconjugate Chemistry*, 7:356-362.

Ozmen et al. (2000) "Infrared fluorescence sensing of submicromolar calcium: pushing the limits of photoinduced electron transfer," *Tetrahedron Letters* 41:9185-9188.

Sun et al.(2006) "'Clickable' Nanoparticles for Targeting Imaging," *Molecular Imaging* 5(2):122-128.

Becker et al. (2000) "Macromolecular Contrast Agents for Optical Imaging of Tumors: Comparison of Indotricarbocyanine-labeled Human Serum Albumin and Transferrin," *Photochem. Photobiol.* 72:234-241.

Brasseur et al. (1999) "Receptor-Mediated Targeting of Phthalocyanines to Macrophages via Covalent Coupling to Native or Maleylated Bovine Serum Albumin," *Photochem. Photobiol.* 69:345-352.

Gatter et al. (1983) "Transferrin Receptors in Human Tissues: Their Distribution and Possible Clinical Relevance," *J. Clin. Path.* 36:539-545.

Hamblin et al. (1994) "Photosensitizer Targeting in Photodynamic Therapy. I. Conjugates of Haematoporphyrin with Albumin and Transferrin," *J. Photochem Photobiol. B.* 26(1):45-56.

Hansch et al. (2004) "Diagnosis of Arthritis Using Near-Infrared Fluorochrome Cy5.5," *Investigative Radiology* 39(10):626-632.

Kremer et al. (2000) "Laser-Induced Fluorescence Detection of Malignant Gliomas Using Fluorescein-labeled Serum Albumin: Experimental and Preliminary Clinical Results," *Neurol. Res.* 22(5):481-489.

Parmelee et al. (1997) "Preclinical Evaluation of the Pharmokinetics, Biodistribution and Elimination of MS-325, a Blood Pool Agent for Magnetic Imaging Resonance," *Investigative Radiology* 32(12):741-747.

Rennen et al. (2001) "The Effect of Molecular Weight on Nonspecific Accumulation of $^{99m}$T-Labeled Proteins in Inflammatory Foci," *Nucl. Med. Biol.* 28(4):401-408.

Schilling et al. (1992) "Design of Compounds Having Enhanced Tumour Uptake, Using Serum Albumin as a Carrier—Part II. In Vivo Studies," *Int. J. Radiat. Appl. Instrum. B.* 19(6):685-695.

Tromberg et al. (1997) "Non-invasive measurements of breast tissue optical properties using frequency-domain photo migration," *Phil. Trans. R. Soc. London B* 352:661-668.

Wang et al.(2001) "Amplified Delivery of Indium-111 to EGFR-Positive Human Breast Cancer Cells," *Nucl. Med. Biol.* 28:895-902.

Williams et al. (1993) "Comparison of Covalent and Noncovalent Labeling with Near-Infrared Dyes for the High-Performance Liquid Chromatographic Determination of Human Serum Albumin," *Anal. Chem.* 65:601-605.

Wyatt (1997) "Cerebral oxygenation and haemodynamics in the fetus and newborn infant," *Phil. Trans. R. Soc. London B* 352:697-700.

Ciernik et al.(1972) "New synthesis of neocyanine dyes containing three heterocycles," *Collection of Czechoslovak Chemical Communications* 37(11):3800-3807. Abstract only.

Ciernik et al.(1972) "New pentamethinecyanine dyes," *Collection of Czechoslovak Chemical Communications* 37(8):2771-2778. Abstract only.

International Search Report and Written Opinion for International Patent Application No. PCT/US2006/034604, dated Jan. 31, 2007, 11 pages.

(56) References Cited

OTHER PUBLICATIONS

Bredereck et al. (1970) "Synthesis in the heterocyclic series. XIV. Formylation of 4-methylpyrimidine and reactions of 2-(4-pyrimidinyl)malonaldehyde," *Justus Liebigs Annalen der Chemie* 737:46-52. Abstract only.
International Search Report of the International Searching Authority for PCT/US2006/034406 dated Feb. 15, 2007, 5 pages.
Written Opinion of the International Searching Authority for PCT/US2006/034406 dated Feb. 15, 2007, 6 pages.
Adams et al. (1998) "Di(1-pyridinio)-und Di)1-bipyridindiio)-dihydrodibenzo[14]annulune," *Anoewandte Chemie* 101(8):1043-1046.
Clayden, J. et al., Organic Chemistry, Oxford University Press: New York, 2001, p. 454-6.

\* cited by examiner

BIOCOMPATIBLE N, N-DISUBSTITUTED SULFONAMIDE-CONTAINING FLUORESCENT DYE LABELS

RELATED APPLICATION(S)

This application claims the benefit of U.S. Provisional Application No. 60/713,632, filed on Sep. 2, 2005.

The entire teachings of the above application are incorporated herein by reference.

BACKGROUND OF THE INVENTION

Optical imaging is an evolving clinical imaging modality that uses penetrating light rays to create images. Light in the red and near-infrared (NIR) range (600-1200 nm) is used to maximize tissue penetration and minimize absorption from natural biological absorbers such as hemoglobin and water. (Wyatt, *Phil. Trans. R. Soc. London B* 352:701-706, 1997; Tromberg, et al., *Phil. Trans. R. Soc. London B* 352:661-667, 1997).

Besides being non-invasive, optical imaging methods offer a number of advantages over other imaging methods: they provide generally high sensitivity, do not require exposure of test subjects or lab personnel to ionizing radiation, can allow for simultaneous use of multiple, distinguishable probes (important in molecular imaging), and offer high temporal and spatial resolution (important in functional imaging and in vivo microscopy, respectively).

In fluorescence imaging, filtered light or a laser with a defined bandwidth is used as a source of excitation light. The excitation light travels through body tissues. When it encounters a reporter molecule (i.e., contrast agent or imaging probe), the excitation light is absorbed. The reporter molecule then emits light that has detectably different properties from the excitation light. The resulting emitted light then can be used to construct an image.

Most optical imaging techniques have relied on the use of organic and inorganic fluorescent molecules as the reporter molecule.

Fluorescent dyes are generally known and used for fluorescence labeling and detection of various biological and non-biological materials by procedures such as fluorescence microscopy, fluorescence immunoassay and flow cytometry. A typical method for labeling such materials with fluorescent dyes is to create a fluorescent complex by means of bonding between suitable groups on the dye molecule and compatible groups on the material to be labeled. In this way, materials such as cells, tissues, amino acids, proteins, antibodies, drugs, hormones, nucleotides, nucleic acids, lipids and polysaccharides and the like may be chemically labeled and detected or quantified, or may be used as fluorescent probes which can bind specifically to target materials and detected by fluorescence detection methods. Brightly fluorescent dyes permit detection or location of the attached materials with great sensitivity.

Certain carbocyanine or polymethine fluorochromes have demonstrated utility as labeling reagents for a variety of biological applications, e.g. U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); also WO 97/40104, WO 99/51702, WO 01/21624, and EP 1 065 250 A1; U.S. Pat. No. 6,448,008 to Caputo et al. and Tetrahedron Letters 41, 9185-88 (2000); all of the above incorporated by reference.

Comprehensive reviews regarding polymethine dyes have been by written by L. G. S. Brooker, "The Theory of the Photographic Process" Mees Ed., Macmillan, N.Y., (1942), p. 987 and (1966), p. 198; Frances M. Hamer, in "The Chemistry of Heterocyclic Compounds", Vol 18, "The Cyanine Dyes and Related Compounds", Weissberger, Ed, Wiley Interscience, New York, (1964); G. E. Ficken, "The Chemistry of Synthetic Dyes", Vol 4, K. Venkataraman Ed., Academic Press, New York, (1971), p. 211; A. I. Kiprianov, Usp. Khim., 29, 1336, (1960), 35, 361 (1966), 40, 594 (1971); D. W. Heseltine, "The Theory of the Photographic Process", 4.sup.th edition, James Ed., Macmillan, N.Y., (1977), chapter 8, "Sensitising and Desensitising Dyes"; S. Daehne, Phot. Sci. Eng., 12, 219 (1979); D. J. Fry, "Rodd's Chemistry of Carbon Compounds", "Cyanine Dyes and Related Compounds", Vol. IVb, chapter 15, p. 369 Elsevier, Amsterdam, (1977); Supplement to Vol. IVb, 2.sup.nd Edition (1985), p. 267; H. Zollinger, "Color Chemistry", VCH, Weinheim (1987), chapters 3 and 14; D. M. Sturmer, "The Chemistry of Heterocyclic Compounds", "Special Topics in Heterocyclic Chemistry", chapter VIII, "Synthesis and Properties of Cyanine and Related Dyes", Weissberger Ed., Wiley, New York, (1977); "The Kirk-Othmer Encyclopaedia of Chemical Technology" Vol 7, p. 782, "Cyanine Dyes", Wiley, New-York, (1993). For many years, polymethine dyes have been very useful as sensitizers in photography, especially in the red and near infrared regions of the spectrum. However, in more recent years, there has been an upsurge of new uses of these dyes in innovative technological areas, such as laser and electro-optic applications, optical recording media, medical, biological and diagnostic. These new applications of polymethine dyes place high demands on the degree of purity required, and the reproducibility of synthetic methods and purification steps is very important.

To be useful as a label, a fluorochrome has to be provided with a suitable side chain containing a functional group. The method and site of introduction of a side chain containing a functional group into the structure for the purpose of conjugation, or binding to another molecule such as a biomolecule (BM), represents the innovative step in the inventions concerning the use of the fluorochrome as a labeling reagent. An approach in the design of polymethine labeling reagents has been to attach the functionalized side arm to one of the heterocyclic moieties ($Z^1$ or $Z^2$), separated by a polymethine linker (PML), of the fluorochrome, of formula (1):

$$Z^1\text{-PML-}Z^2 \tag{1}$$

Another approach in the design of polymethine labeling reagents has been to attach the functionalized side arm to one of the heterocyclic moieties (for example $Z^2$), separated by a polymethine linker (PML), of the fluorochrome, of formula (1a):

$$Z^2\text{-PML-}Z^2 \tag{1a}$$

See, for instance: J. S. Lindsey, P. A. Brown, and D. A. Siesel, "Visible Light Harvesting in Covalently-Linked Porphyrin-Cyanine Dyes, Tetrahedron, 45, 4845, (1989); R. B. Mujumdar, L. A. Ernst, S. R. Mujumdar, and A. S. Waggoner, "Cyanine Dye Labelling Reagents Containing Isothiocyanate Groups", Cytometry, 10, 11 (1989); L. A. Ernst, R. K. Gupta, R. B. Mujumdar, and A. S. Waggoner, "Cyanine Dye Labelling Reagents for sulphydryl Groups", Cytometry, 10, 3, (1989); P. L. Southwick P. L., L. A. Ernst, E. W. Tauriello, S. R. Parker, R. B. Mujumdar, S. R. Mujumdar, H. A. Clever, and A. S. Waggoner, "Cyanine Dye Labelling Reagents-Carboxymethylindocyanine Succinimidyl Esters", Cytometry 11, 418 (1990); R. B. Mujumdar, L. A. Ernst, Swati R. Mujumdar, C. J. Lewis, and A. S. Waggoner, "Cyanine Dye Labelling Reagents: Sulfoindocyanine Succinimidyl Esters", Bioconjugate Chemistry, 4, 105, (1993); A. J. G. Mank, E. J. Molenaar, H. Lingeman, C. Goojer, U.

A. Th. Brinkman, and N. H. Velthorst, "Visible Diode Laser Induced Fluorescence Detection in Liquid Chromatography after Precolumn Derivatisation of Thiols", Anal. Chem., 65, 2197, (1993); H. Yu., J. Chao, D. Patek, S. R. Mujumdar, and A. S. Waggoner, "Cyanine dye dUTP analogs for enzymatic labelling of DNA Probes", Nucl. Acids Res 22, 3226, (1994); A. J. G. Mank, H. T. C. van der Laan, H. Lingeman, Cees Goojer, U. A. Th. Brinkman, and N. H. Velthorst, "Visible Diode Laser-Induced Fluorescence Detection in Liquid Chromatography after Precolumn Derivatisation of Amines", Anal. Chem., 67, 1742, (1995); S. R. Mujumdar, R. B. Mujumdar, C. M. Grant, and A. S. Waggoner, "Cyanine Labelling Reagents: sulfobenzoindocyanine succinimidyl esters", Bioconjugate Chemistry, 7, 356, (1996). Patent Literature: P. L. Southwick, and A. S. Waggoner, "Intermediate for and Fluorescent Cyanine Dyes containing Carboxylic Acid Groups", U.S. Pat. No. 4,981,977, Jan. 1, 1991; A. S. Waggoner, L. A. Ernst, and Mujumdar, R. B., "Method for Labelling and Detecting Materials Employing Arylsulfonate Cyanine Dyes", U.S. Pat. No. 5,268,486, Dec. 7., 1993; A. S. Waggoner, "Cyanine Dyes as Labelling Reagents for Detection of Biological and Other Materials by Luminescence Methods", U.S. Pat. No. 5,627,027, May 6, 1996; A. S. Waggoner, and R. B. Mujumdar, "Rigidised Trimethine Cyanine Dyes", WO99/311181; G.-Y. Shen, T. S. Dobashi, "Cyanine Dye Activating Group with Improved Coupling Selectivity"; G. M. Little, R. Raghavachari; N. Narayanan; H. L. Osterman, "Fluorescent Cyanine Dyes", U.S. Pat. No. 6,027,709, Feb. 22, 2000.

The general synthetic strategy necessary to prepare these labeling reagents is as follows. First, a quaternized nitrogen heterocycle $Z^1$ is prepared. Then, this heterocyclic base is reacted with a polymethine linker (PML) that is an electrophilic reagent such as PhNH—(CH=CH)$_n$—CH=NHPh.HCl or RO—(CH=CH)$_n$—CH(OR)$_2$, where Ph is a phenyl ring and R a methyl or ethyl group, to obtain hemicyanines such as, $Z^1$—(CH=CH)$_n$—CH=NHPh or $Z^1$—(CH=CH)$_n$—CH=NAcPh (where Ac is the acetyl radical) or $Z^1$—(CH=CH)$_n$—OR. These intermediates are then reacted with a different quaternary nitrogen heterocycle, $Z^2$. The functionalized side arm is attached either to the first ($Z^1$) or to the second ($Z^2$) quaternized nitrogen heterocycle. The final result is a non-symmetric polymethine labeling reagent, $Z^1$-PML-$Z^2$. Examples of hemicyanine intermediates are described in F. M. Hamer, "Some Unsymmetrical Pentamethincyanine Dyes and their Tetramethin Intermediates", J. Chem. Soc., 32 (1949) and R. B. Mujumdar, L. A. Ernst, Swati R. Mujumdar, C. J. Lewis, and A. S. Waggoner, "Cyanine Dye Labelling Reagents: Sulfoindocyanine Succinimidyl Esters", Bioconjugate Chemistry, 4, 105, (1993).

Polymethine fluorochromes that are efficient and easy to produce as well as suitable for preparing conjugates with biomolecules are desirable.

SUMMARY OF THE INVENTION

The present inventors succeeded in synthesizing polymethine fluorochromes as described in In one embodiment the present invention is directed to a compound represented by formula (2):

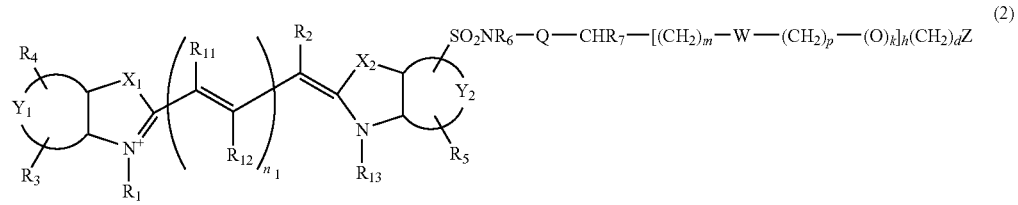

or a salt thereof.

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, halogen, alkyl, alkoxy, aryloxy, aryl, a sulfonate, a group containing $SO_2NR_6$-Q-CHR$_7$—(CH$_2$)$_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are —H, (CH$_2$)$_x$CH$_3$, when x is an integer selected from 0 to 6; or $R_1$ and $R_{13}$ are independently (CH$_2$)$_n$SO$_3^-$ or (CH$_2$)$_n$SO$_3$H when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or NR$_6$, Q and CHR$_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl, with the proviso that the compound is not Y$_1$ and Y$_2$ are each independently a benzo-condensed ring, a naphtha-condensed ring or a pyrido-condensed ring;

n$_1$ is 1, 2, or 3;

R$_2$, R$_{11}$ and R$_{12}$ are independently H, F, Br, Cl, C$_1$-C$_6$ alkyl, C$_1$-C$_6$ alkoxy, aryloxy, a nitrogen-containing heterocyclic ring, a nitrogen-containing heteroaromatic ring, a sulfonate, an iminium ion, or any two adjacent R$_{12}$ and R$_{11}$ substituents or R$_2$ and R$_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by C$_1$-C$_6$ alkyl, halogen, or OR* or SR*;

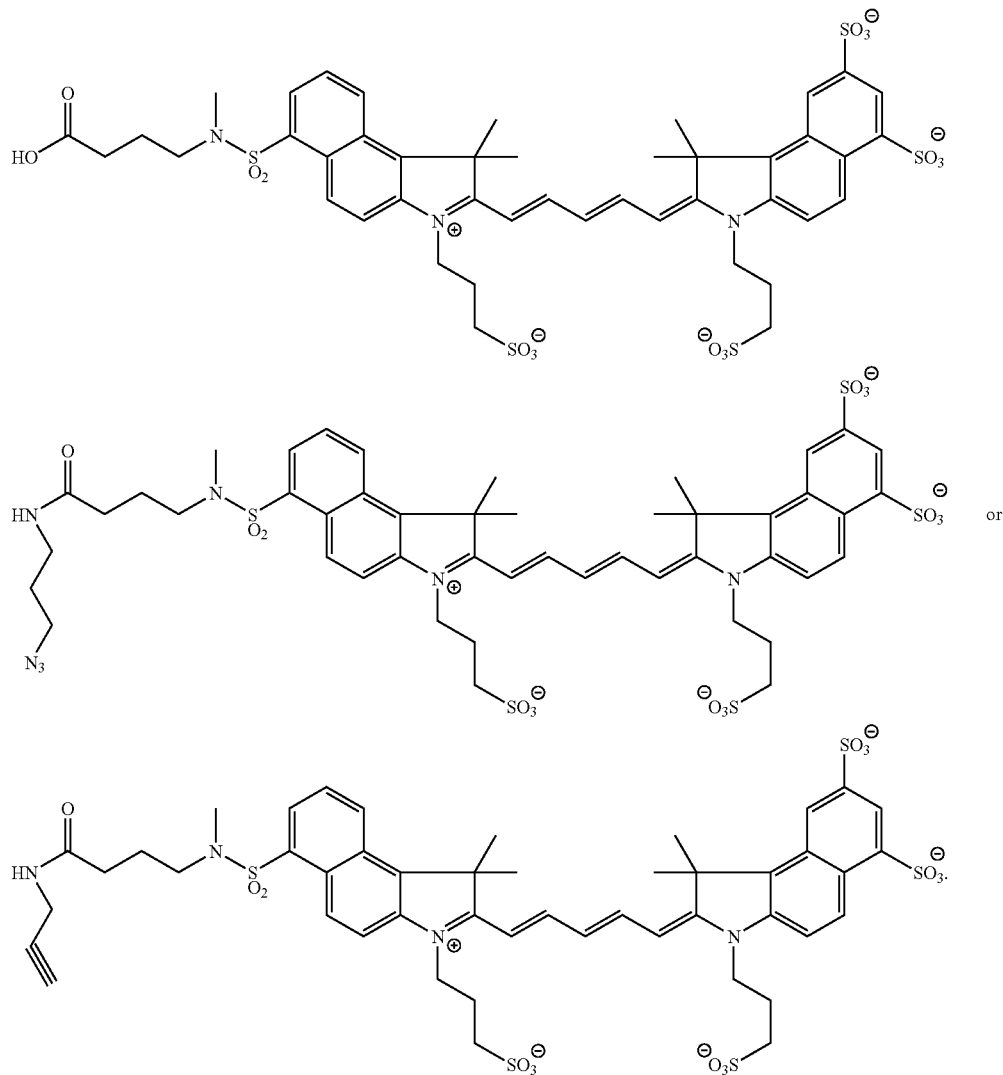

In another embodiment the present invention is directed to a compound represented by formula (2) or a salt thereof wherein X$_1$ and X$_2$ are independently selected from the group consisting of C(CH$_2$K$_1$)(CH$_2$K$_2$), O, S and Se;

K$_1$ and K$_2$ are independently selected from the group consisting of H, a C$_1$-C$_{20}$ aliphatic group and a C$_1$-C$_{20}$ aliphatic group substituted with —OR*, N(R*)$_2$ or —SR*; or K$_1$ and K$_2$ together are part of a substituted or unsubstituted carbocyclic, or heterocyclic ring;

R$_1$ and R$_{13}$ are (CH$_2$)$_x$CH$_3$, when x is an integer selected from 0 to 6; or R$_1$ and R$_{13}$ are independently (CH$_2$)$_n$SO$_3^-$ or (CH$_2$)$_n$SO$_3$H when n is an integer selected from 2 to 6;

R$_3$, R$_4$ and R$_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

R$_6$ is selected from the group consisting of a substituted or unsubstituted C$_1$-C$_{20}$ aliphatic group, a substituted or unsubstituted aryl, a substituted or unsubstituted alkylaryl, wherein $R_6$ is optionally substituted with halogen, OR*, $N(R^*)_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, $N(R^*)_2$ or SR*; or $R_6$ and $R_7$, taken together form a 4-, 5-, 6- or 7-membered heterocyclic or non-aromatic heterocyclic ring optionally substituted with halogen, OR*, $N(R^*)_2$ or SR*; or $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, $N(R^*)_2$ or —SR*; and W is absent or is a group selected from the group consisting of —$SO_2NR_6$-Q-$CHR_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In another embodiment the present invention is directed to a compound represented by formula (2) or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, $N(R^*)_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring; $n_1$ is 1, 2, or 3;

$R_2$, $R_{11}$ and $R_{12}$ are independently H, halogen, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, a group containing $SO_2NR_6$-Q-$CHR_7$—$(CH_2)_m$; i is 0 or 1; and m=0-12 or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, $N(R^*)_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, $N(R^*)_2$ or SR*; or $R_6$ and $R_7$, taken together form a 4-, 5-, 6- or 7-membered heterocyclic or non-aromatic heterocyclic ling optionally substituted with halogen, OR*, $N(R^*)_2$ or SR*; or $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, $N(R^*)_2$ or —SR*; and W is absent or is a group selected from the group consisting of —$SO_2NR_6$-Q-$CHR_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In another embodiment the present invention is directed to a compound represented by formula (2) or a salt thereof, wherein $X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, $N(R^*)_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring; $n_1$ is 1, 2, or 3;

$R_2$, $R_{11}$ and $R_{12}$ are independently a group containing $SO_2NR_6$-Q-$CHR_7$—$(CH_2)_m$; i is 0 or 1; and m=0-12, alkyl, aryl, alkoxy, halogen, S-aryl or S-alkyl, $R_1$ and $R_{13}$ are H;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, $N(R^*)_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, $N(R^*)_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —SO$_2$NR$_6$-Q-CHR$_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In another embodiment the present invention is directed to a biocompatible fluorescent molecule comprising one or more biomolecules chemically linked to a compound of the present invention.

In another embodiment the present invention is directed to a biocompatible fluorescent molecule comprising a biomolecule chemically linked to a compound of the present invention wherein the compound has an absorption and emission maxima between about 400 nm and about 900 nm.

In another embodiment the present invention is directed to a biocompatible fluorescent molecule comprising a biomolecule chemically linked to a compound of the present invention wherein the compound is activated after target interaction.

In another embodiment the present invention is directed to a biocompatible fluorescent molecule comprising a biomolecule chemically linked to a compound of the present invention wherein the compound has a high binding affinity to a target.

In another embodiment the present invention is directed to a method of in vivo optical imaging, the method comprising:

(a) administering to a subject one or more compounds or biocompatible fluorescent molecules of the present invention (b) allowing time for the compound or biocompatible fluorescent molecule to distribute within the subject or to contact or interact with a biological target;

(c) illuminating the subject with light of a wavelength absorbable by the compound or biocompatible fluorescent molecule; and (d) detecting the optical signal emitted by the compound or biocompatible fluorescent molecule.

In another embodiment the present invention is directed to a biocompatible fluorescent molecule comprising a biomolecule chemically linked to a compound of the present invention wherein the biomolecule is a labeled cell.

DETAILED DESCRIPTION OF THE INVENTION

Figure 1:
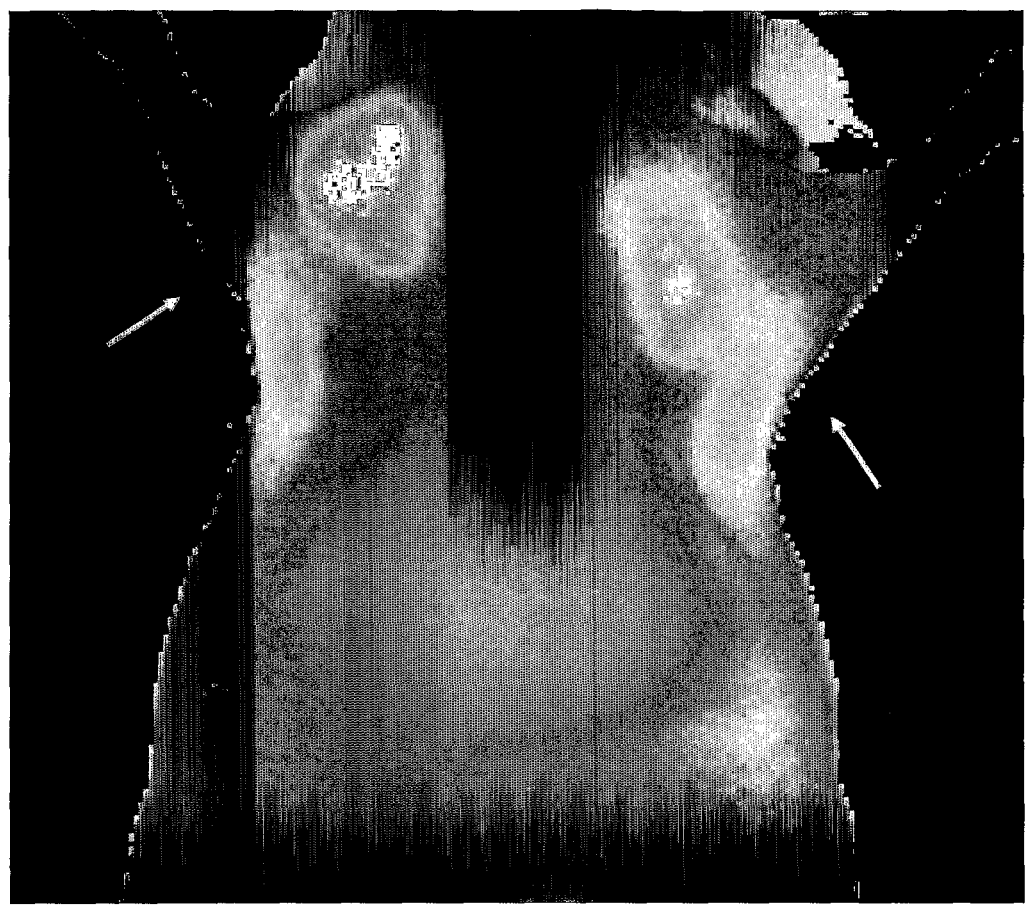
FIG. 1 is a fluorescence image of a compound of the present invention in tumors of a female NU/NU mice (6-8 weeks old) after 24 hrs on a fluorescence reflectance system (FRI, Kodak 2000MM) system.
Figure 2:
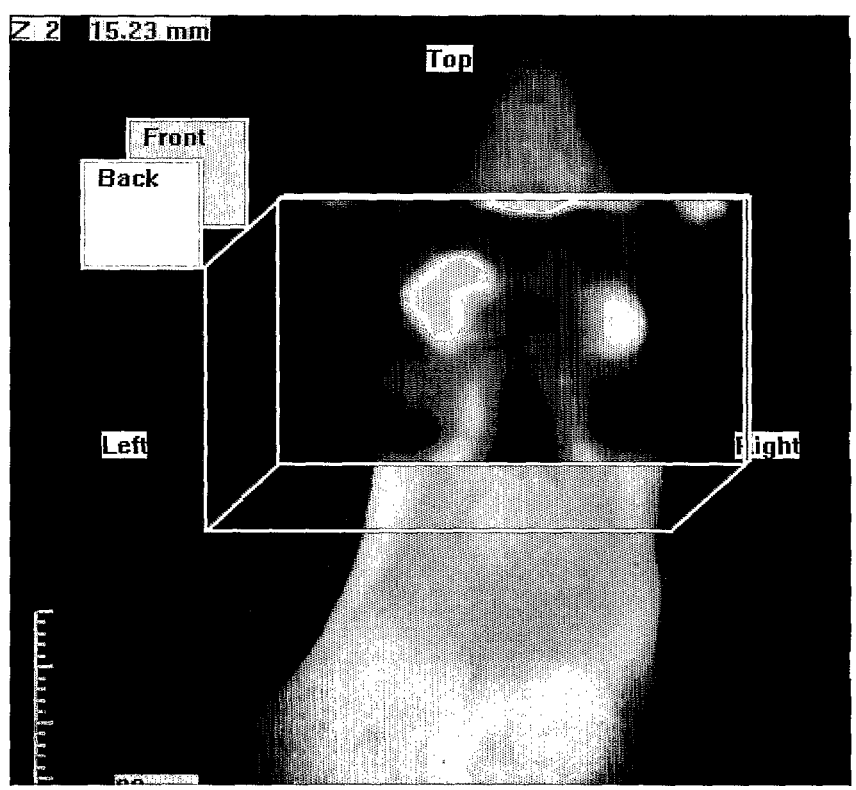
FIG. 2 is a fluorescence image of a compound of the present invention in tumors of a female NU/NU mice (6-8 weeks old) after 24 hrs on a fluorescence reflectance system VisEn's Fluorescence Tomography System (FMT).
Figure 3:
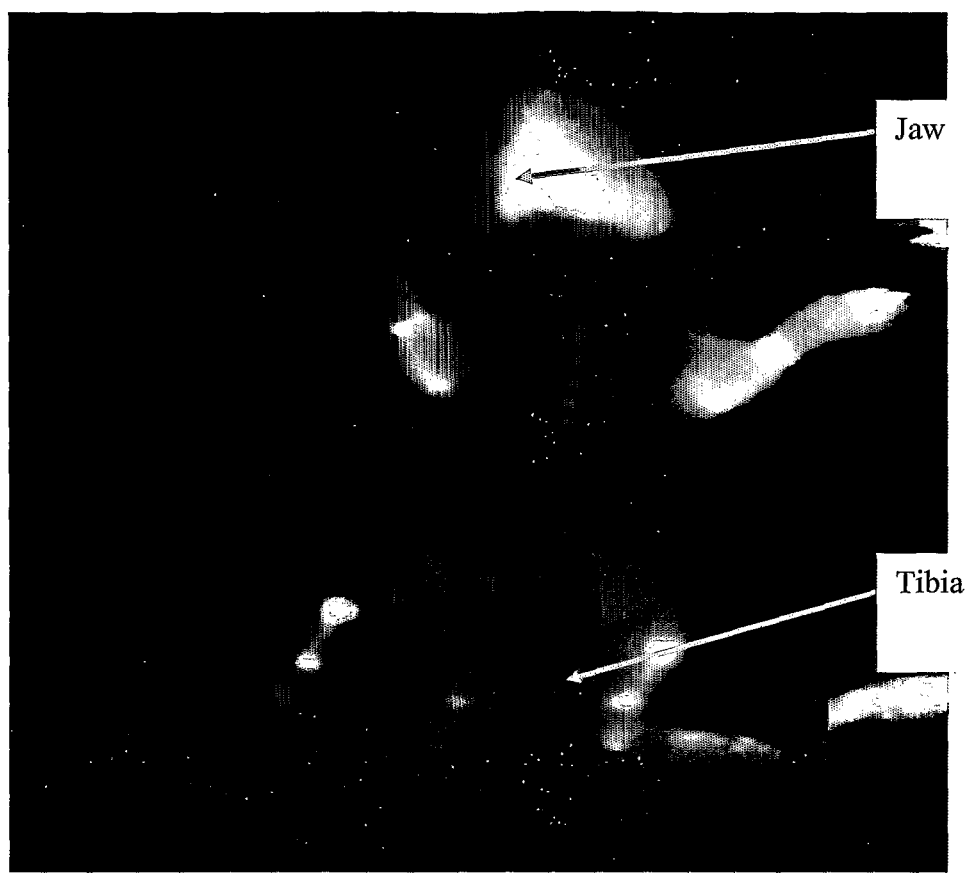
FIG. 3 is a fluorescence image bone growth of Five day-old BALB/c×CF-1 F$_1$ mice which were injected with a compound of the present invention after 24 hrs later using a fluorescence reflectance imaging (FRI) system (Kodak 2000MM).

A description of preferred embodiments of the invention follows.

The present invention is directed to bright, highly fluorescent compounds (dyes) that absorb and/or emit between about 440 and about 1100 nm, between about 550 and about 800 nm, between about 500 and about 900 m or between about 600 and about 900 nm and conjugates thereof. It will be appreciated that compounds (fluorochromes) with excitation and emission wavelengths in other spectrums, such as the visible and ultraviolet light spectrum, are also encompassed by the present invention.

The structures of the compounds of the present invention, in general are based on N,N-disubstituted sulfonamide side arm derivatives that confer high fluorescence. Moreover, in certain embodiments of the present invention the compounds contain functional or reactive groups which may be used to chemically link with complementary groups on target molecules.

"Chemically linked" means connected by an attractive force between atoms strong enough to allow the combined aggregate to function as a unit. This includes, but is not limited to, chemical bonds such as covalent bonds, non-covalent bonds such as ionic bonds, metallic bonds, and bridge bonds, hydrophobic interactions, hydrogen bonds, and van der Waals interactions. This also includes cross-linking or caging.

The term "compounds," as used herein, refers to "polymethine fluorochromes", "fluoro chromes", "fluorescent dyes", "cyanine dyes" "carbocyanine dyes" and "dyes" of the instant invention. These terms are used interchangeably to refer to the compounds of the instant invention.

In one embodiment, the compounds of the invention comprise two heterocyclic ring systems bound together by a polymethine linker (PML), according to the formula (1):

$$Z^1\text{-(PML)-}Z^2 \tag{1}$$

wherein $Z^1$ is a heterocyclic ring system, such as, an indolinium ring, $Z^2$ is a second heterocyclic ring system, such as, an indolinium ring, and PML is a polymethine linker. The $Z^1$ and $Z^2$ ring systems are optionally further substituted by a variety of substituents or are fused to additional rings that are optionally further substituted. The substituents are introduced to enhance optical and physical properties of the fluorochromes as well as to incorporate a functional side arm for chemically linking to biomolecules.

In one aspect, the compounds of the present invention are further substituted one or more times by sulfo or sulfoalkyl. By "sulfo" is meant sulfonic acid, or salt of sulfonic acid (sulfonate). Similarly, by "carboxyl" is meant carboxylic acid, carboxylate ester or salt of carboxylic acid. "Phosphate" is an ester of phosphoric acid, and includes salts of phosphate. "Phosphonate" means phosphonic acid and includes salts of phosphonate. Similarly for "carbonyl" groups such as, but not limited to carbonyl halode, (e.g., chloride) and carboxamide are included. As used herein, unless otherwise specified, the alkyl portions of substituents such as alkyl, alkoxy, arylalkyl, alkylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

In one embodiment, the present invention is directed to compounds represented by formula (2) or a salt thereof:

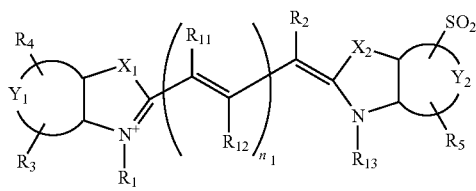

(2)

wherein $X_1$, $X_2$ are independently selected from the group $C(CH_2K_1)(CH_2K_2)$, O, S, Se. $K_1$ and $K_2$ are independently selected from H and $C_1$-$C_{20}$ alkyl that is linear or branched, saturated or unsaturated, optionally containing N, S, O in various forms; or independently wherein $K_1$ and $K_2$ together are part of a cyclic ring optionally further substituted. $Y_1$, $Y_2$ are nonmetal atoms required to form a benzo-condensed ring or a naphtha-condensed ring or a pyrido-condensed ring and $n_1$ is 1, 2, or 3. $R_2$, $R_{11}$ and $R_{12}$ are independently H, F, Br, Cl, $C_1$-$C_6$ alkyl, $C_1$-$C_6$ alkoxy, aryloxy, a nitrogen heterocycle, a sulfonate, an iminium ion, or any two adjacent $R_{12}$ or $R_{11}$ substituents or $R_2$ and $R_{11}$ substituents, when taken in combination, forms a 4-, 5-, or 6-membered saturated or unsaturated hydrocarbon ring that is optionally substituted one or more times by $C_1$-$C_6$ alkyl, halogen, or O or S-bearing moiety. $R_1$ and $R_{13}$ are selected from the group consisting of H, $(CH_2)_nCH_3$, $(CH_2)_nSO_3$— and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3$— or $(CH_2)_nSO_3H$. $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety. $R_6$ is independently selected from $C_1$-$C_{20}$ alkyl that is linear or branched, saturated or unsaturated, aryl, alkylaryl, optionally containing halogens, N, S, O in various forms; $R_7$ is independently selected from H, $C_1$-$C_{20}$ alkyl that is linear or branched, saturated or unsaturated, aryl, alkylaryl, optionally containing halogens, N, S, O in various forms; $R_6$ and $R_7$, when taken in combination, forms a 4-, 5-, 6- or 7-membered saturated or unsaturated hydrocarbon ring optionally containing halogens, N, S, O in various forms. Q is absent, $C_1$-$C_6$ alkyl, $C_1$-$C_6$ cycloalkyl, wherein the alkyl or cyclic group contains 0-2 hetero atoms selected from N, O, S. The cyclic group may incorporate $NR_6$ and $CHR_7$ as a part of the ring system. Q is carbonyl (CO) and $R_6$ is independently selected from H, $C_1$-$C_{20}$ alkyl that is linear or branched, saturated or unsaturated, aryl, alkylaryl, optionally containing halogens, N, S, O in various forms.

W is either absent or is a group selected from —$SO_2NR_6$-Q-$CHR_7$—, —O—, —COO—, and —CONH—. Also, h=0-70; k=0 or 1; d=0-12; m=0-12; p=0-12. Z is, or contains a N, O or S nucleophile functionality or is, or contains a functionality capable of reacting with N, O or S nucleophiles. Such compounds of formula (2) are chemically linked to biocompatible fluorescent molecules for a variety of applications including in vivo imaging.

In another embodiment, the present invention is directed to compounds represented by formula (2) or a salt thereof:

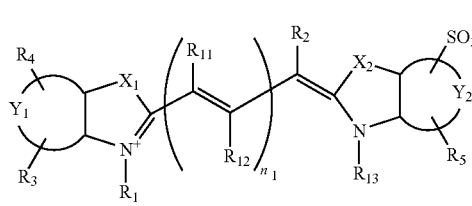

(2)

wherein $X_1$, $X_2$ are independently selected from the group $C(CH_2K_1)(CH_2K_2)$, O, S, Se. $K_1$ and $K_2$ are independently selected from H and $C_1$-$C_{20}$ alkyl that is linear or branched, saturated or unsaturated, optionally containing N, S, O in various forms; or independently wherein $K_1$ and $K_2$ together are part of a cyclic ring optionally further substituted. $Y_1$, $Y_2$ are nonmetal atoms required to form a benzo-condensed ring or a naphtha-condensed ring or a pyrido-condensed ring and $n_1$ is 1, 2, or 3. $R_2$, $R_{11}$ and $R_{12}$ are independently H, F, Br, Cl, $C_1$-$C_6$ alkyl, $C_1$-$C_6$ alkoxy, aryloxy, a nitrogen heterocycle, a sulfonate, an iminium ion, or any two adjacent $R_{12}$ or $R_{11}$ substituents or $R_2$ and $R_{11}$ or $R_2$ and $R_{12}$ substituents, when taken in combination, forms a 4-, 5-, or 6-membered saturated or unsaturated hydrocarbon ring that is optionally substituted one or more times by $C_1$-$C_6$ alkyl, halogen, or O or S-bearing moiety. $R_1$ and $R_{13}$ are selected from the group consisting of $(CH_2)_nCH_3$, $(CH_2)_nSO_3$— and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3$— or $(CH_2)_nSO_3H$. $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety. $R_6$ is independently selected from $C_1$-$C_{20}$ alkyl that is linear or branched, saturated or unsaturated, aryl, alkylaryl, optionally containing halogens, N, S, O in various forms; $R_7$ is independently selected from H, $C_1$-$C_{20}$ alkyl that is linear or branched, saturated or unsaturated, aryl, alkylaryl, optionally containing halogens, N, S, O in various forms; $R_6$ and $R_7$, when taken in combination, forms a 4-, 5-, 6- or 7-membered saturated or unsaturated hydrocarbon ring optionally containing halogens, N, S, O in various forms. Q is absent, $C_1$-$C_6$ alkyl, $C_1$-$C_6$ cycloalkyl, wherein the alkyl or cyclic group contains 0-2 hetero atoms selected from N, O, S. The cyclic group may incorporate $NR_6$ and $CHR_7$ as a part of the ring system. Q is carbonyl (CO) and $R_6$ is independently selected from H, $C_1$-$C_{20}$ alkyl that is linear or branched, saturated or unsaturated, aryl, alkylaryl, optionally containing halogens, N, S, O in various forms.

W is either absent or is a group selected from —$SO_2NR_6$-Q-$CHR_7$—, —O—, —COO—, and —CONH—. Also, h=0-70; k=0 or 1; d=0-12; m=0-12; p=0-12. Z is, or contains a N, O or S nucleophile functionality or is, or contains a functionality capable of reacting with N, O or S nucleophiles. Such compounds of formula (2) are chemically linked to biocompatible fluorescent molecules for a variety of applications including in vivo imaging.

In one embodiment, the present invention is directed to compounds representing $Z^1$-(PML)-$Z^2$ by the formula:

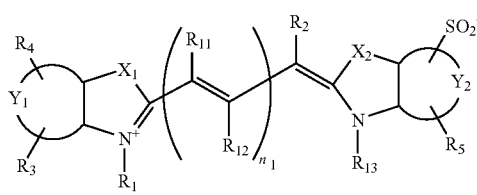

(2)

or a salt thereof, wherein:

$Y_1$, $Y_2$ are nonmetal atoms required to form a benzo-condensed ring or a naphtha-condensed ring or a pyrido-condensed ring.

In one embodiment $Y_1$, $Y_2$ represent the atoms necessary to form one to two fused aromatic rings having 6 atoms in each ring, which atoms are selected from —CH, —C, —$CR_8$, and —$NR_9$, where $R_9$ is 0 or 1 (such that each ring nitrogen is either quaternized or not), and each $R_8$ independently contains sulfo, trifluoromethyl, or halogen; $R_9$ independently contains a $C_1$-$C_8$ alkyl, in turn containing independently an H, amino or sulfo.

Incorporation of one or more non-hydrogen substituents on the fused rings can be used to tune the absorption and emission spectrum of the resulting dye.

Selected examples of the basic structure of $Z^1$ in formulae (1) and (2) are shown below. These basic structures are optionally further substituted.

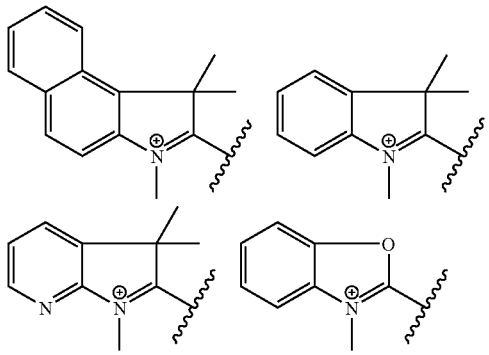

In one embodiment in formula (2) $X_1$, $X_2$ are independently selected from $C(CH_2K_1)(CH_2K_2)$, O, S, Se, wherein $K_1$ and $K_2$ are independently selected from H and $C_1$-$C_{20}$ alkyl that is linear or branched, saturated or unsaturated, optionally containing N, S, O in various forms; or independently wherein $K_1$ and $K_2$ together are part of a cyclic ring or X is independently selected from —$CR_{20}OR_{21}$, wherein $R_{20}$ and $R_{21}$, which may be the same or different, are alkyl, cycloalkyl, or arylalkyl, together part of a cyclic system and optionally further substituted.

In one aspect of the invention, for compounds represented by formula (2) $R_3$ and $R_4$ taken in combination complete a five or six-membered ring.

In one embodiment in compounds represented by formula (2) $R_1$ and $R_{13}$ are selected from the group consisting of H, $(CH_2)_nCH_3$, $(CH_2)_nSO_3$— and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3$— or $(CH_2)_nSO_3H$. In one aspect of the invention $R_1$ and $R_{13}$ are substituents containing an aryl sulfonate or an amino group or a phthalimido group.

In one embodiment in compounds represented by formula (2) $R_1$ and $R_{13}$ are selected from the group consisting of $(CH_2)_nCH_3$, $(CH_2)_nSO_3$— and $(CH_2)_nSO_3H$, wherein n is an integer selected from 0 to 6 when $R_1$ or $R_{13}$ is $(CH_2)_nCH_3$, and n is an integer selected from 2 to 6 when $R_1$ or $R_{13}$ is $(CH_2)_nSO_3$— or $(CH_2)_nSO_3H$. In one aspect of the invention $R_1$ and $R_{13}$ are substituents containing an aryl sulfonate or an amino group or a phthalimido group.

The substituents $R_3$, $R_4$ and $R_5$ in compounds represented by formula (2) are independently selected from the group H, halogens, carboxylate, carboxylic acid, carboxylic esters, amino, amide, alkyl or aryl sulfonamide, hydroxy, alkoxy, aryloxy, sulfate, cyano, nitro, azido, alkylamino, dialkylamino, trialkylammonium, phosphate, phosphate ester, phosphonate, sulphonic acid and a sulphonate moiety.

In one embodiment, the compounds of the present invention are sulfonated one or more times. If the compound of the present invention is substituted by sulfo (that is, for example, a sulfonic acid moiety, sulfonate moiety or sulfonamamide), it is typically sulfonated at $R_3$ or $R_4$ or $R_5$ or all, or sulfoalkylated independently at each $R_1$ or $R_{13}$ or both (that is, for example, $(CH_2)_nSO_3^-$ or $(CH_2)_nSO_3OH$), or is both sulfonated and sulfoalkylated.

As used herein the terms sulfonic acid and $(CH_2)_nSO_3H$ or a sulfonate group and $(CH_2)_nSO_3^-$ can be used interchangeably. However in certain embodiments the terms a sulfonic acid moiety, sulfonate moiety or sulfonamamide refer to substituents which are attached to the remainder of the molecule by the a sulfonic acid moiety, sulfonate moiety or sulfonamamide moiety, ie., —$SO_2NR'R''$.

In one embodiment the present invention is directed to a compound represented by structural formula (2):

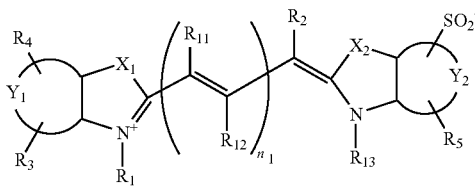

(2)

or a salt thereof.

$X_1$ and $X_2$ are independently selected from the group consisting of $C(CH_2K_1)(CH_2K_2)$, O, S and Se. In one embodiment $X_1$ and $X_2$ are independently $C(CH_2K_1)(CH_2K_2)$.

$K_1$ and $K_2$ are independently selected from the group consisting of H, a $C_1$-$C_{20}$ aliphatic group and a $C_1$-$C_{20}$ aliphatic group substituted with —OR*, $N(R^*)_2$ or —SR*; or $K_1$ and $K_2$ together are part of a substituted or unsubstituted carbocyclic or heterocyclic ring. In one embodiment, $K_1$ and $K_2$ are independently H or a $C_1$-$C_{20}$ alkyl group. In one embodiment $K_1$ and $K_2$ are independently H or a $C_1$-$C_{10}$ alkyl group. In one embodiment $K_1$ and $K_2$ are independently H or a $C_1$-$C_{40}$ alkyl group.

$Y_1$ and $Y_2$ are each independently a benzo-condensed ring, a naphtha-condensed ring or a pyrido-condensed ring.

$n_1$ is 1, 2, or 3.

$R_2$, $R_{11}$ and $R_{12}$ are independently H, halogen, alkyl, alkoxy, aryloxy, aryl, a sulfonate, a group containing $SO_2NR_6$-Q-$CHR_7$—$(CH_2)_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring. In one embodiment the carbocyclic rings are each independently optionally substituted one or more times by $C_1$-$C_6$ alkyl, halogen, or OR* or SR*. In one embodiment, $R_2$, $R_{11}$ and $R_{12}$ are independently H, alkyl, aryl, a sulfonate, a group containing $SO_2NR_6$-Q-$CHR_7$—$(CH_2)_m$; i is 0 or 1; and m=0-12, an iminium ion, S-aryl, S-alkyl, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*. In one embodiment, $R_2$, $R_{11}$ and $R_{12}$ are independently H, $C_{1-20}$ alkyl, a sulfonate, a group containing $SO_2NR_6$-Q-$CHR_7$—$(CH_2)_m$; i is 0 or 1; and m=0-12, or any two adjacent $R_{12}$ and $R_{11}$ substituents or $R_2$ and $R_{11}$ substituents, when taken in combination, form a 4-, 5-, or 6-membered carbocyclic ring, non-aromatic carbocyclic ring or carbocyclic aryl ring.

$R_1$ and $R_{13}$ are —H, $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6.

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety. In one embodiment, $R_3$, $R_4$ and $R_5$ are independently selected from the group consisting of H, sulfonamide, a sulphonic acid moiety and a sulphonate moiety. In certain embodiments, $R_3$, $R_4$ and $R_5$ are independently, sulphonic acid or a salt thereof.

$R_6$ is selected from the group consisting of a substituted or unsubstituted $C_1$-$C_{20}$ aliphatic group, a substituted or unsubstituted aryl, a substituted or unsubstituted alkylaryl, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms. In one embodiment $R_6$ is optionally substituted with halogen, OR*, $N(R^*)_2$ or SR*. In another embodiment Q is optionally substituted with —OR*, $N(R^*)_2$ or —SR*. In one embodiment $R_6$ is selected from the group consisting of a $C_1$-$C_{20}$ alkyl group, an aryl, an alkylaryl, when Q is absent, a carbonyl group a $C_1$-$C_6$ alkyl group, or a $C_1$-$C_6$ carbocyclic, non-aromatic carbocyclic, heterocyclic or non-aromatic heterocyclic ring. In one embodiment $R_6$ is a $C_1$-$C_{10}$ alkyl group, when Q is absent, a carbonyl group a $C_1$-$C_6$ alkyl group, or a $C_1$-$C_6$ carbocyclic, non-aromatic carbocyclic, heterocyclic or non-aromatic heterocyclic ring.

Alternatively $R_6$ is H, when Q is a carbonyl.

$R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, $N(R^*)_2$ or SR*. In one embodiment $R_7$ is optionally substituted with halogen, OR*, $N(R^*)_2$ or SR*. In one embodiment $R_7$ is selected from the group consisting of H, a $C_1$-$C_{20}$ alkyl group, an aryl, an alkylaryl. In one embodiment $R_7$ is selected from the group consisting of H, or a $C_1$-$C_{10}$ alkyl group; or Alternatively, $R_6$ and $R_7$, taken together form a 4-, 5-, 6- or 7-membered heterocyclic or non-aromatic heterocyclic ring. In one embodiment the carbocyclic, heterocyclic, non-aromatic carbocyclic or aryl ring is optionally substituted with halogen, OR*, $N(R^*)_2$ or SR*. In one embodiment, $R_6$ and $R_7$, when taken in combination, form a 4-, 5-, 6- or 7-membered carbocyclic, heterocyclic, non-aromatic carbocyclic or aryl ring.

Alternatively, $NR_6$, Q and $CHR_7$ together form a substituted or unsubstituted or heterocyclic or non-aromatic heterocyclic ring system wherein the rings contain 1 or 2 heteroatoms. In one embodiment the carbocyclic, heterocyclic, non-aromatic carbocyclic or aryl ring is optionally substituted with halogen, OR*, $N(R^*)_2$ or SR*. In one embodiment, $R_6$ and $R_7$, when taken in combination, form a 4-, 5-, 6- or 7-membered carbocyclic, heterocyclic, non-aromatic carbocyclic or aryl ring.

W is absent or is a group selected from the group consisting of —$SO_2NR_6$-Q-$CHR_7$—, —O—, —COO—, and —CONH—. In one embodiment, W is absent.

h=0-70; k=0 or 1; d=0-12; m=0-12; p=0-12. In one embodiment h=0-10; k=0 or 1; d=0-6; m=0-6; p=0-6.

Z is, or contains a N, O or S nucleophile functionality or is, or contains a functionality capable of reacting with N, O or S nucleophiles; and each R* is independently —H or C1-20 alkyl. In one embodiment each R* is independently —H or C1-10 alkyl.

In one embodiment, for compounds represented by formula (2):

$R_1$ and $R_{13}$ are —H; and the group —$((C(R_{11})=C(R_{12}))_{n1}$—$C(R_2)=$ is represented by a structural formula selected from the group consisting of:

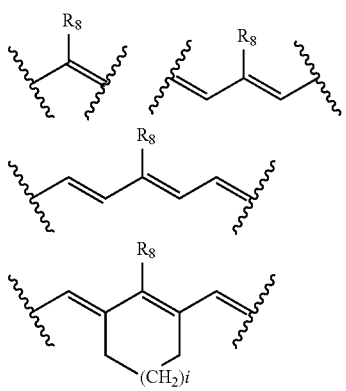

wherein $R_8$ is selected from the group consisting of H, a halogen atom, S-aryl, S-alkyl, alkyl, aryl, alkoxy, aryloxy and a group containing $SO_2NR_6$-Q-$CHR_7$—$(CH_2)_m$; i is 0 or 1; and m=0-12; and the remainder of the variables are as described above.

In certain embodiments for compounds represented by formula (2) Z is a nucleophile functionality selected from the group consisting of —$NH_2$, —OH, and —SH, and the remainder of the variables are as described above.

In certain other embodiment for compounds represented by formula (2) Z is a functionality capable of reacting with N, O, S nucleophiles selected from the group consisting of —COCl, —(CO)O(CO)R, —$CONHNH_2$, substituted and unsubstituted N-hydroxysuccinimido esters, nitro- or fluoro-phenol esters, —NCS, —CHO, —$COCH_2I$, phosphoramidite and maleimide group, and the remainder of the variables are as described above. In one embodiment the nucleophile is selected from the group consisting of —COCl, —(CO)O(CO)R, —$CONHNH_2$, substituted and unsubstituted N-hydroxysuccinimido esters, —NCS, —CHO, —$COCH_2I$, phosphoramidite and maleimide group.

In another embodiment the present invention is directed to a compound represented by structural formula (2):

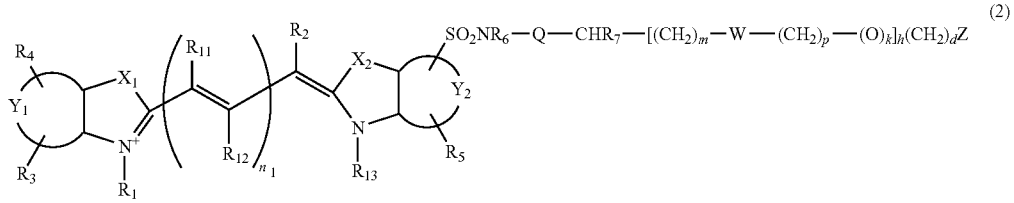

or a salt thereof.

$X_1$ and $X_2$ are independently selected from the group consisting of $C(CH_2K_1)(CH_2K_2)$, O, S and Se. In one embodiment $X_1$ and $X_2$ are independently $C(CH_2K_1)(CH_2K_2)$.

$K_1$ and $K_2$ are independently selected from the group consisting of H, a $C_1$-$C_{20}$ aliphatic group and a $C_1$-$C_{20}$ aliphatic group substituted with —OR*, $N(R*)_2$ or —SR*; or $K_1$ and $K_2$ together are part of a substituted or unsubstituted carbocyclic, or heterocyclic ring. In one embodiment, $K_1$ and $K_2$ are independently H or a $C_1$-$C_{20}$ alkyl group. In one embodiment $K_1$ and $K_2$ are independently H or a $C_1$-$C_{10}$ alkyl group. In one embodiment $K_1$ and $K_2$ are independently H or a $C_1$-$C_{40}$ alkyl group.

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, F, Br, Cl, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring. In one embodiment the carbocyclic rings are each independently optionally substituted one or more times by $C_1$-$C_6$ alkyl, halogen, or OR* or SR*. In one embodiment, $R_2$, $R_{11}$ and $R_{12}$ are independently H, $C_1$-$C_6$ alkyl, a nitrogen-containing heterocyclic ring, a nitrogen-containing heteroaromatic ring, or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*. In one embodiment, $R_2$, $R_{11}$ and $R_{12}$ are independently H, $C_{1-6}$ alkyl, a nitrogen-containing heterocyclic ring, or any two adjacent $R_{12}$ and $R_{11}$ substituents or $R_2$ and $R_{11}$ substituents, when taken in combination, form a 4-, 5-, or 6-membered carbocyclic ring, non-aromatic carbocyclic ring or carbocyclic aryl ring.

$R_1$ and $R_{13}$ are $(CH_2)_xCH_3$, when x is an integer selected from 0 to 6; or $R_1$ and $R_{13}$ are independently $(CH_2)_nSO_3^-$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety. In one embodiment, $R_3$, $R_4$ and $R_5$ are independently selected from the group consisting of H, sulfonamide, a sulphonic acid moiety and a sulphonate moiety. In certain embodiments, $R_3$, $R_4$ and $R_5$ are independently, sulphonic acid or a salt thereof.

$R_6$ is selected from the group consisting of a substituted or unsubstituted $C_1$-$C_{20}$ aliphatic group, a substituted or unsubstituted aryl, a substituted or unsubstituted alkylaryl, when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms. In one embodiment $R_6$ is optionally substituted with halogen, OR*, N(R*)$_2$ or SR*. In another embodiment Q is optionally substituted with —OR*, N(R*)$_2$ or —SR*. In one embodiment $R_6$ is selected from the group consisting of a $C_1$-$C_{20}$ alkyl group, an aryl, an alkylaryl, when Q is absent, a carbonyl group a $C_1$-$C_6$ alkyl group, or a $C_1$-$C_6$ carbocyclic, non-aromatic carbocyclic, heterocyclic or non-aromatic heterocyclic ring. In one embodiment $R_6$ is a $C_1$-$C_{10}$ alkyl group, when Q is absent, a carbonyl group a $C_1$-$C_6$ alkyl group, or a $C_1$-$C_6$ carbocyclic, non-aromatic carbocyclic, heterocyclic or non-aromatic heterocyclic ring.

Alternatively $R_6$ is H, when Q is a carbonyl.

$R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*. In one embodiment $R_7$ is optionally substituted with halogen, OR*, N(R*)$_2$ or SR*. In one embodiment $R_7$ is selected from the group consisting of H, a $C_1$-$C_{20}$ alkyl group, an aryl, an alkylaryl. In one embodiment $R_7$ is selected from the group consisting of H, or a $C_1$-$C_{10}$ alkyl group; or Alternatively, $R_6$ and $R_7$, taken together form a 4-, 5-, 6- or 7-membered heterocyclic or non-aromatic heterocyclic ring. In one embodiment the carbocyclic, heterocyclic, non-aromatic carbocyclic or aryl ring is optionally substituted with halogen, OR*, N(R*)$_2$ or SR*. In one embodiment, $R_6$ and $R_7$, when taken in combination, form a 4-, 5-, 6- or 7-membered carbocyclic, heterocyclic, non-aromatic carbocyclic or aryl ring.

Alternatively, $NR_6$, Q and $CHR_7$ together form a substituted or unsubstituted or heterocyclic or non-aromatic heterocyclic ring system wherein the rings contain 1 or 2 heteroatoms. In one embodiment the carbocyclic, heterocyclic, non-aromatic carbocyclic or aryl ring is optionally substituted with halogen, OR*, N(R*)$_2$ or SR*. In one embodiment, $R_6$ and $R_7$, when taken in combination, form a 4-, 5-, 6- or 7-membered carbocyclic, heterocyclic, non-aromatic carbocyclic or aryl ring.

W is absent or is a group selected from the group consisting of —SO$_2$NR$_6$-Q-CHR$_7$—, —O—, —COO—, and —CONH—. In one embodiment, W is absent.

h=0-70; k=0 or 1; d=0-12; m=0-12; p=0-12. In one embodiment h=0-10; k=0 or 1; d=0-6; m=0-6; p=0-6.

Z is, or contains a N, O or S nucleophile functionality or is, or contains a functionality capable of reacting with N, O or S nucleophiles; and each R* is independently —H or C1-20 alkyl. In one embodiment each R* is independently —H or C1-10 alkyl.

In certain embodiments for compounds represented by formula (2) Z is a nucleophile functionality selected from the group consisting of —NH$_2$, —OH, and —SH, and the remainder of the variables are as described above.

In certain other embodiment for compounds represented by formula (2) Z is a functionality capable of reacting with N, O, S nucleophiles selected from the group consisting of —COCl, —(CO)O(CO)R, —CONHNH$_2$, substituted and unsubstituted N-hydroxysuccinimido esters, nitro- or fluorophenol esters, —NCS, —CHO, —COCH$_2$I, phosphoramidite and maleimide group, and the remainder of the variables are as described above. In one embodiment the nucleophile is selected from the group consisting of —COCl, —(CO)O(CO)R, —CONHNH$_2$, substituted and unsubstituted N-hydroxysuccinimido esters, —NCS, —CHO, —COCH$_2$I, phosphoramidite and maleimide group.

In one embodiment of the present invention, for compounds represented by formula (2) as described in the preceding thirty six paragraphs at least two of the groups $R_1$, $R_3$, $R_4$, $R_5$ or $R_{13}$ contain a sulfonic acid or a sulfonate group.

In one embodiment of the present invention, for compounds represented by formula (2) as described in the preceding thirty seven paragraphs $R_3$, $R_4$ and $R_5$ are each independently a group of the formula —SO$_2$NR$_6$-Q-CHR$_7$—[(CH$_2$)$_m$—W—(CH$_2$)$_p$—(O)$_k$]$_h$—(CH$_2$)$_d$Z.

In one embodiment of the present invention, for compounds represented by formula (2) as described in the preceding thirty eight paragraphs one of $R_3$, $R_4$ and $R_5$ is —SO$_2$NR$_6$-Q-CHR$_7$—[(CH$_2$)$_m$—W—(CH$_2$)$_p$—(O)$_k$]$_h$—(CH$_2$)$_d$Z.

In one embodiment of the present invention, for compounds represented by formula (2) as described in the preceding thirty nine paragraphs $X_1$ and $X_2$ are both —C(CH$_3$)$_2$ In one embodiment of the present invention, for compounds represented by formula (2) as described in the preceding forty paragraphs the group —((C(R$_{11}$)═C(R$_{12}$))$_{n1}$—C(R$_2$)═ is represented by a structural formula selected from the group consisting of:

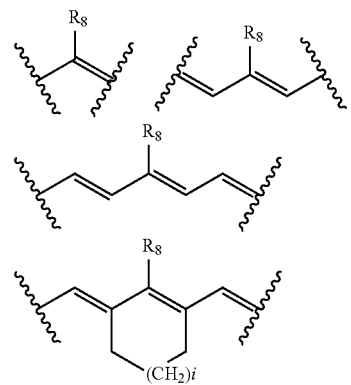

wherein $R_8$ is selected from the group consisting of H or Cl, Br or F.

In certain embodiment the compound of the present invention is represented by any one of the formulae 3-5:

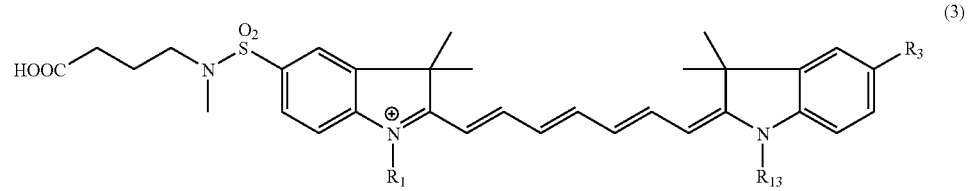

(3)

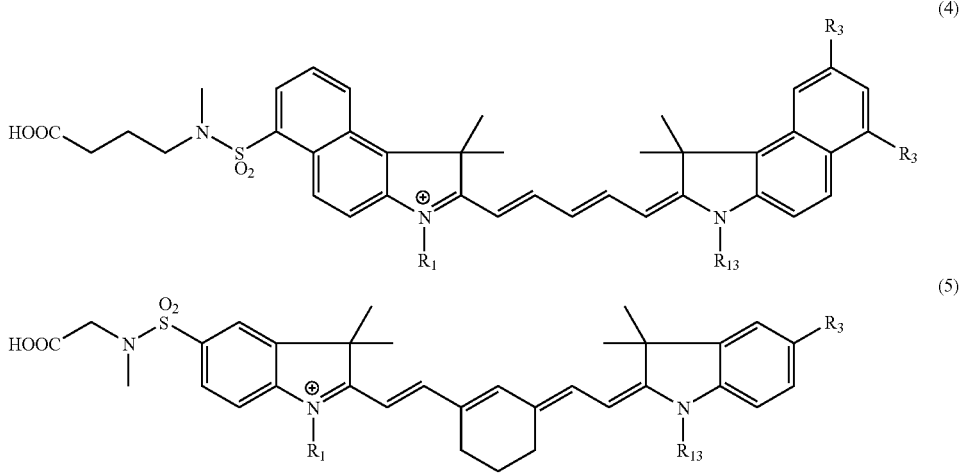

(4)

(5)

wherein:

$R_1$ and $R_{13}$ are independently selected from the group consisting of $(CH_2)_xCH_3$, $(CH_2)_nSO_3{-}$ and $(CH_2)_nSO_3H$; wherein x is an integer selected from 0 to 6 and n is an integer selected from 2 to 6.

$R_3$ is selected from the group consisting of H, carboxylate, carboxylic acid, carboxylic ester, amine, amide, sulfonamide, hydroxyl, alkoxyl, a sulphonic acid moiety and a sulphonate moiety.

In one embodiment the present invention is directed to a compound represented by structural formula (2):

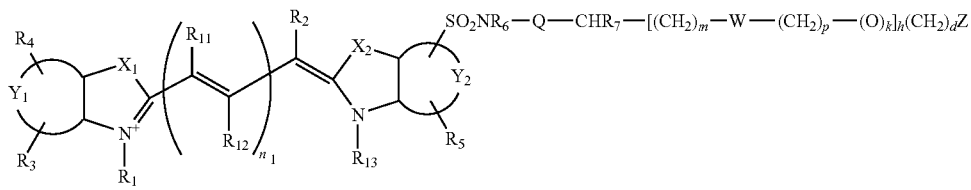

or a salt thereof, wherein:

$X_1$ and $X_2$ are independently selected from the group consisting of $C(CH_2K_1)(CH_2K_2)$, O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently H, halogen, $C_1$-$C_6$ alkyl, $C_1$-$C_6$ alkoxy, aryloxy, a nitrogen-containing heterocyclic ring, a nitrogen-containing heteroaromatic ring, a sulfonate, an iminium ion, a group containing $SO_2NR_6$-Q-$CHR_7$—$(CH_2)_m$; i is 0 or 1; and m=0-12 or any two adjacent $R_{12}$ and $R_{11}$ substituents or $R_2$ and $R_{11}$ substituents, when taken in combination, form a 4-, 5-, or 6-membered substituted or unsubstituted carbocyclic ring, substituted or unsubstituted non-aromatic carbocyclic ring or a substituted or unsubstituted carbocyclic aryl ring, wherein the carbocyclic rings are each independently optionally substituted one or more times by $C_1$-$C_6$ alkyl, halogen, or OR* or SR*;

$R_1$ and $R_{13}$ are $(CH_2)_xCH_3$, when x is an integer selected from 0 to 6; or $R_1$ and $R_{13}$ are independently $(CH_2)_nSO_3{-}$ or $(CH_2)_nSO_3H$ when n is an integer selected from 2 to 6;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR* when Q is absent, a carbonyl group a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic or heterocyclic ring wherein the ring may incorporate $NR_6$ and $CHR_7$ as a part of the ring system and the heterocyclic ring contains 0-2 heteroatoms, wherein Q is optionally substituted with —OR*, N(R*)$_2$ or —SR*; or $R_6$ is H, when Q is a carbonyl;

$R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*;

or $R_6$ and $R_7$, when taken in combination, form a 4-, 5-, 6- or 7-membered carbocyclic, heterocyclic, non-aromatic carbocyclic or aryl optionally substituted with halogen, OR*, N(R*)$_2$ or SR*;

W is absent or is a group selected from the group consisting of —$SO_2NR_6$-Q-$CHR_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, Q or S nucleophiles; and each R* is independently —H or C1-20 alkyl.

In certain embodiments, the group —((C($R_{11}$)=C($R_{12}$))$_{n1}$—C($R_2$)= is represented by a structural formula selected from the group consisting of:

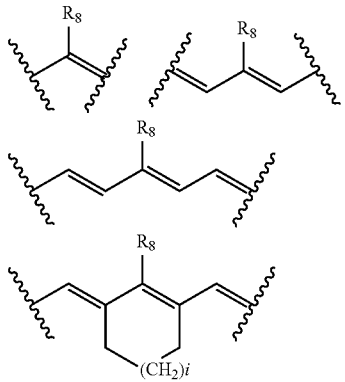

wherein $R_8$ is selected from the group consisting of H, a halogen atom, and a group containing $SO_2NR_6$-Q-$CHR_7$—$(CH_2)_m$; i is 0 or 1; and m=0-12, and the remainder of the variables are as described immediately above.

In one embodiment the present invention is directed to a compound represented by structural formula (2):

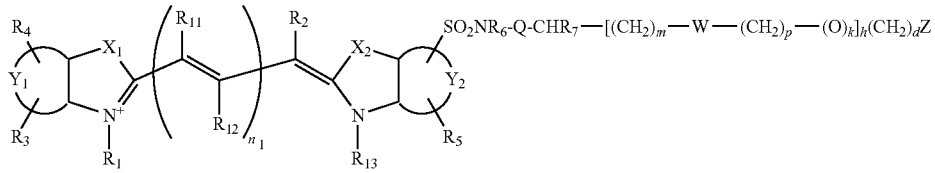

or a salt thereof, wherein:

$X_1$ and $X_2$ are independently selected from the group consisting of C($CH_2K_1$)($CH_2K_2$), O, S and Se;

$K_1$ and $K_2$ are independently selected from the group consisting of H, a $C_1$-$C_{20}$ aliphatic group and a $C_1$-$C_{20}$ aliphatic group substituted with —OR*, N(R*)$_2$ or —SR*; or $K_1$ and $K_2$ together are part of a substituted or unsubstituted carbocyclic, or heterocyclic ring;

$Y_1$ and $Y_2$ are each independently a benzo-condensed ring, a naphtha-condensed ring or a pyrido-condensed ring;

$n_1$ is 1, 2, or 3;

$R_2$, $R_{11}$ and $R_{12}$ are independently a group containing $SO_2NR_6$-Q-$CHR_7$—$(CH_2)_m$; i is 0 or 1; and m=0-12, alkyl, aryl, alkoxy, halogen, S-aryl or S-alkyl, $R_1$ and $R_{13}$ are H;

$R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;

$R_6$ is selected from the group consisting of a substituted or unsubstituted $C_1$-$C_{20}$ aliphatic group, a substituted or unsubstituted aryl, a substituted or unsubstituted alkylaryl, wherein $R_6$ is optionally substituted with halogen, OR*, N(R*)$_2$ or SR* when Q is absent, a carbonyl group, a substituted or unsubstituted $C_1$-$C_6$ alkyl group, wherein 0-2 of the methylene groups of the alkyl group are replaced by NH, O or S, or a substituted or unsubstituted $C_1$-$C_6$ carbocyclic, non-aromatic carbocyclic, heterocyclic or non-aromatic heterocyclic ring wherein the heterocyclic rings contains 1-2 heteroatoms; or $R_6$ is H, when Q is a carbonyl; and $R_7$ is selected from the group consisting of H, a substituted or unsubstituted $C_1$-$C_{20}$ aliphatic group, a substituted or unsubstituted aryl, a substituted or unsubstituted alkylaryl, wherein $R_7$ is optionally substituted with halogen, OR*, N(R*)$_2$ or SR*; or $R_6$ and $R_7$, taken together form a 4-, 5-, 6- or 7-membered heterocyclic or non-aromatic heterocyclic ring optionally substituted with halogen, OR*, N(R*)$_2$ or SR*; or $NR_6$, Q and $CHR_7$ together form a substituted or unsubstituted or heterocyclic or non-aromatic heterocyclic ring system wherein the rings contain 1 or 2 heteroatoms, wherein rings are optionally substituted with —OR*, N(R*)$_2$ or —SR*; and W is absent or is a group selected from the group consisting of —$SO_2NR_6$-Q-$CHR_7$—, —O—, —COO—, and —CONH—;

h=0-70; k=0 or 1; d=0-12; m=0-12; p=0-12;

Z is, or contains a N, O or S nucleophile functionality or is, or contains a functionality capable of reacting with N, O or S nucleophiles; and each R* is independently —H or C1-20 alkyl.

In certain embodiments of the present invention $R_2$, $R_{11}$ and $R_{12}$ are independently, S-aryl or S-alkyl, and the remainder of the variables are as described immediately above.

Suitable examples of appropriate PML moieties for the compounds of the present invention (carbocyanine dyes) have been previously described in the literature, including PML moieties that incorporate nonhydrogen substituents, ring structures, and rigidizing elements (U.S. Pat. No. 5,831,098 to Ollmann, Jr (1998); U.S. Pat. No. 6,086,737 to Patonay et al. (2000); U.S. Pat. No. 6,048,982 to Waggoner (2000); and U.S. Pat. No. 5,453,505 to Lee et al. (1995); U.S. Pat. No. 5,639,874 to Middendorf et al. (1997); U.S. Pat. No. 3,864,644 to Lincoln et al (1975); U.S. Pat. No. 4,011,086 to Simson (1977); U.S. Pat. No. 6,747,159 to Caputo (2004); all incorporated by reference).

In one embodiment of the present invention a reactive group (or chemically linked molecule) can be attached to $Y_2$, in certain compounds (indocyanine dyes) of the present invention. In addition to a reactive group at $Y_2$, the compounds may be additionally sulfonated at least four times (at $R_3$ and $R_4$, and as sulfoalkyl at both $R_1$ and $R_{13}$). In one embodiment of the present invention a reactive group (or chemically linked molecule) can be attached to $Y_2$, in certain compounds (indocyanine dyes) of the present invention. In addition to a reactive group at $Y_2$, the compounds may be additionally sulfonated up to four times (at $R_3$ and $R_4$, and as sulfoalkyl at both $R_1$ and $R_{13}$). This extra sulfonation, results in reactive dyes and dye conjugates that have novel properties, such as, for example, improved aqueous solubility.

As used herein, "reactive group" means a moiety on a compound of the present invention or that can be added to a compound of the present invention that is capable of chemically reacting with a functional group on a different compound to form a covalent linkage, or a moiety on a different compound that is capable of chemically reacting with a functional group on compound of the present invention to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the compound of the present invention and the substance to be conjugated results in one or more atoms of the reactive group to be incorporated into a new linkage attaching the dye to the conjugated substance.

The PML moiety typically originates from the coupling agent used in the synthesis of the compounds (dye) of the present invention. For example, N,N'-diphenylformamidine and triethylorthoformate yields PML moieties. Malonaldehyde bis(phenylimine) hydrochloride, 1,1,3-trimethoxypropane, and 1,1,3,3-tetramethoxypropane and glutaconaldehyde dianil monochloride also yield dyes.

The choice of the PML, which is in effect the choice of $n_1$ and $R_2$, $R_{12}$, $R_{11}$ may also affect the absorption and fluorescence properties of the fluorochrome. The length of the PML between $Z^1$ and $Z^2$ also affects the absorption and fluorescence properties of the fluorochrome. Where $n_1=1$, and the indolium heterocycle is not fused to additional rings, the resulting fluorochromes typically exhibits an absorption maximum near 550 nm. Where $n_1=2$, the fluorochromes typically absorb maximally near 650 nm. The fluorochromes, where $n_1=3$, typically absorbs maximally near 750 nm.

In one aspect of the invention, $n_1$ is 1, 2, or 3; $R_2$, $R_{11}$ and $R_{12}$ are independently H, F, Br, Cl, $C_1$-$C_6$ alkyl, $C_1$-$C_6$ alkoxy, aryloxy, a nitrogen heterocycle, a sulfonate, an iminium ion, or any two adjacent $R_{12}$ or $R_{11}$ substituents or $R_2$ and $R_{11}$ substituents, when taken in combination, forms a 4-, 5-, or 6-membered saturated or unsaturated hydrocarbon ring that is optionally substituted one or more times by $C_1$-$C_6$ alkyl, halogen, or O or S-bearing moiety.

One aspect of the invention is a compound of formula (2), wherein only one $R_{12}$ is selected from a group consisting of a functionalized nitrogen-containing heterocyclic ring (substituted nitrogen containing heteroaryl ring). In this embodiment, heterocyclic ring and heteroaryl ring refers to heteroaryl ring as defined herein, such as pyridine and functionalized refers to substituted.

Another aspect of the invention is a compound of formula (2), wherein only one $R_{12}$ is selected from a group consisting of a pyridine ring.

In one aspect of the invention, the PML moiety is introduced into the dye using the malonodialdehyde moieties shown below:

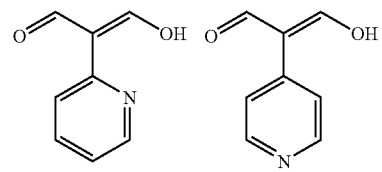

In one aspect of the invention the pyridine nitrogen, on the PML, can be quaternized to modify the physical and pharmacological properties of the compounds of the present invention.

The functional side arm can be introduced in either $Z^1$ or $Z^2$. The functional side arm is positioned anywhere in the moiety described by $Y_1$ or $Y_2$.

In one aspect of the invention, the formula $Z^1$-(PML)-$Z^2$ is represented according to the following:

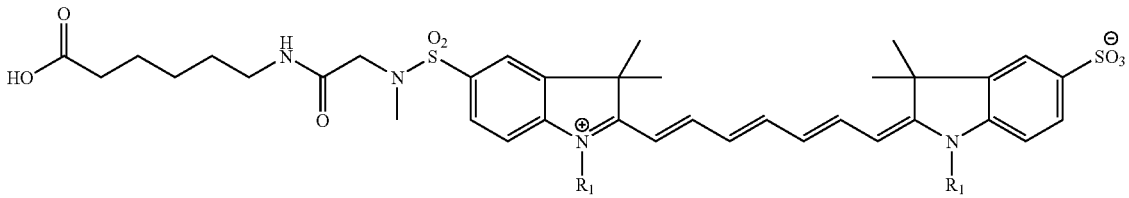

wherein each $R_1$ is independently selected from the group consisting of $(CH_2)_xCH_3$, $(CH_2)_nSO_3^-$ and $(CH_2)_nSO_3H$; wherein x is an integer selected from 0 to 6 and n is an integer selected from 2 to 6.

The functional side arm is typically introduced by the reaction of an appropriately amine functionalized side arm to a sulfonyl chloride group on $Y_1$ or $Y_2$. The amine functionalized side arm may exist in the form of an amine salt.

In one embodiment the amine functional side arm used to couple to the sulfonyl chloride on $Y_1$ or $Y_2$ is a hydrochloride salt. Thus, $R_6$ is independently selected from $C_1$-$C_{20}$ alkyl that is linear or branched, saturated or unsaturated, aryl, alkylaryl, optionally containing halogens, N, S, O in various forms.

In one aspect of the invention $R_6$ is a methyl group. Thus, $R_7$ is independently selected from H, $C_1$-$C_{20}$ alkyl that is linear or branched, saturated or unsaturated, aryl, alkylaryl, optionally containing halogens, N, S, O in various forms.

In one aspect Q is absent. In another aspect Q is $C_1$-$C_6$ alkyl. In another embodiment Q is $C_1$-$C_6$ cycloalkyl, wherein the alkyl or cyclic group contains 0-2 hetero atoms selected from N, O, S. The cyclic group may incorporate $NR_6$ and $CHR_7$ as a part of the ring system. In a further aspect Q is carbonyl (CO) and $R_6$ is independently selected from H, $C_1$-$C_{20}$ alkyl that is linear or branched, saturated or unsaturated, aryl, alkylaryl, optionally containing halogens, N, S, O in various forms.

In one embodiment the moiety —$SO_2NR_6$-Q-$CHR_7$— is of formula:

In another aspect of the invention, Q, $R_6$ and $R_7$, when taken in combination, forms a 4-, 5-, 6- or 7-membered saturated or unsaturated hydrocarbon ring optionally containing halogens, N, S, O in various forms.

In one embodiment the moiety —$SO_2NR_6$-Q-$CHR_7$— is of formula:

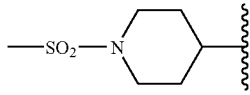

In one aspect of the invention, the moiety —$SO_2NR_6$-Q-$CHR_7$-Z, when m=0, p=0, k=0, h=0, and d=0, is prepared from cyclic-alpha-amino acids such as proline, hydroxyproline, 1,2,3,4-tetrahydroisoquinoline-3-carboxylic acid and the appropriate sulfonyl chloride.

In one aspect of the invention, the moiety —$SO_2NR_6$-Q-$CHR_7$— is of formula:

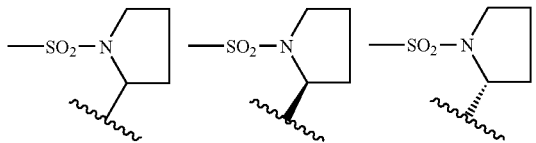

In one aspect of the invention, the moiety —$SO_2NR_6$-Q-$CHR_7$— is of formula:

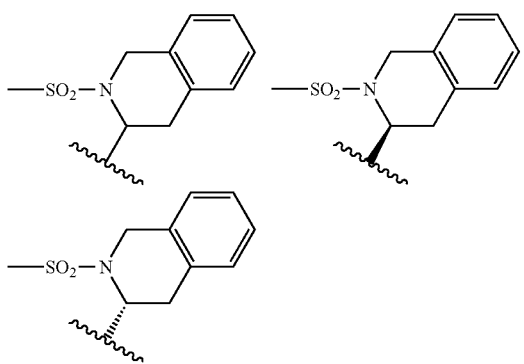

W is either absent or is a group selected from —$SO_2NR_6$-Q-$CHR_7$—, —O—, —COO—, and —CONH—.

In one aspect of the invention, the values of h=0-70; k=0 or 1; d=0-12; m=0-12; p=0-12.

In one aspect, Z is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. In another aspect of the invention, Z is a succinimidyl ester of a carboxylic acid, a maleimide, an iodoacetamide or a succinimidyl ester of a carboxylic acid. In a further aspect of the invention, Z is independently a nucleophile functionality selected from the group consisting of —$NH_2$, —OH, and —SH. Furthermore, Z can be a functionality capable of reacting with N, O, S nucleophiles including but not limited to the group consisting of —COCl, —(CO)O(CO)R, —$CONHNH_2$, substituted and unsubstituted N-hydroxysuccinimido esters, —NCS, —CHO, —$COCH_2I$, phosphoramidite and maleimide group.

In one aspect of the invention, Z=CO—$OR_{15}$ or Z=CO—$R_{16}$ and is in the form of an activated ester ($R_{15}$) or carbonyl halide ($R_{16}$=F, Cl, Br) that is capable of reacting with nucleophiles. The carboxyl group CO—$OR_{15}$ is also in a form selected from the group CO-Obenzotriazolyl, CO—ON-hydroxysuccinimidyl, CO-Otetrafluorophenyl, CO-Opentafluorophenyl, CO-Oimidazolyl, CO-Op-nitrophenyl.

In one aspect of the invention, Z=CO—$OR_{15}$ or Z=CO—$R_{16}$ and is in the form of an activated ester ($R_{15}$) or carbonyl halide ($R_{16}$=F, Cl, Br) that is capable of reacting with nucleophiles. The carboxyl group CO—$OR_{15}$ is also in a form selected from the group CO-Obenzotriazolyl, CO—ON-succinimidyl, CO-Otetrafluorophenyl, CO-Opentafluorophenyl, CO-Oimidazolyl, CO-Op-nitrophenyl.

In one aspect of the invention, Z is an azide. In another aspect of the invention Z is an alkyne.

In one aspect of the invention when Z is an activated ester, the compound can be chemically linked to bifunctional linkers such as aminoethylmaleimide, aminopropylmaleimide, aminopropylazide, aminopropylthiol, mercaptoethylamine, propargylamine 3-aminopropanol, diaminopropane, and diaminobutane to provide additional reactive functional groups in a suitable solvent under neutral or basic conditions.

In one aspect of the invention when Z is $NH_2$, the compound of the invention can be chemically linked to bifunctional linkers such as propargylic acid, succinimidylpyridinedithiopropionate, maleimide-PEG-N-hydroxysuccinimide ester to provide additional reactive functional groups in a suitable solvent under neutral or basic conditions.

In one aspect of the invention, the formula $Z^1$-(PML)-$Z^2$ is represented according to the following, wherein at least two of the groups $R_1$, $R_3$, $R_4$, $R_5$ or $R_{13}$ contain a sulfonic acid or a sulfonate group.

In one aspect of the invention, the formula $Z^1$-(PML)-$Z^2$ is represented according to the following, wherein $R_3$, $R_4$ and $R_5$ are independently all a group of the formula —$SO_2NR_6$-Q-$CHR_7$—[$(CH_2)_m$—W—$(CH_2)_p$—$(O)_k]_h$—$(CH_2)_d$Z.

In one aspect of the invention, the formula $Z^1$-(PML)-$Z^2$ is represented according to the following, wherein $X_1$ and $X_2$ are both —$C(CH_3)_2$.

In one aspect of the invention, the formula $Z^1$-(PML)-$Z^2$ is represented according to the following, wherein the polymethine linker having from 3 to 7 carbon atoms is selected from the group consisting of:

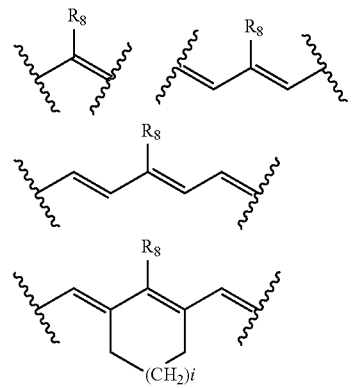

wherein $R_8$ is selected from the group consisting of H, a halogen atom, the group —S-aryl, S-alkyl, alkyl, aryl, alkoxy, aryloxy, and a group containing $SO_2NR_6$-Q-$CHR_7$—$(CH_2)_m$ and i is 0 or 1; m=0-12.

In one aspect of the invention, the formula $Z^1$-(PML)-$Z^2$ is represented according to the following, wherein the polymethine linker having from 3 to 7 carbon atoms as show above wherein $R_8$ is H:

In one aspect of the invention, the formula $Z^1$-(PML)-$Z^2$ is represented according to the following, wherein the polymethine linker having from 3 to 7 carbon atoms is selected from the group consisting of:

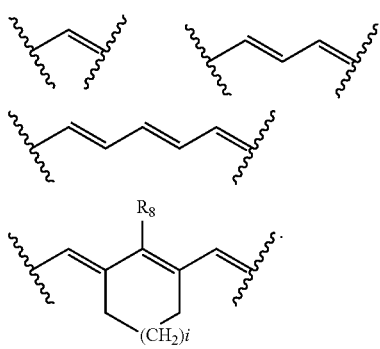

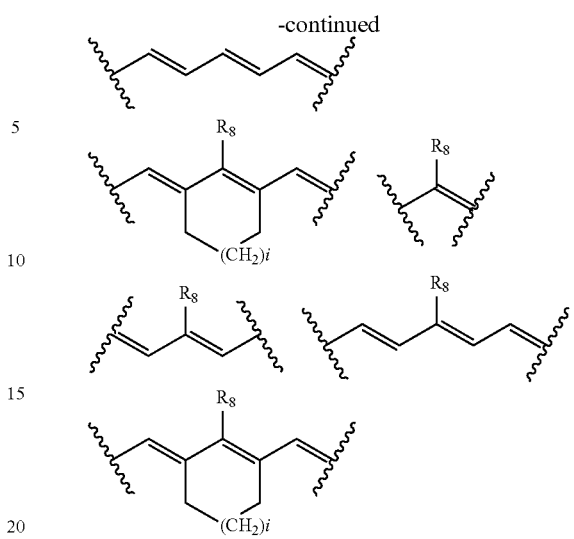

wherein $R_8$ is selected from the group consisting of H, a halogen atom, the group and a group containing $SO_2NR_6$-Q-$CHR_7$—$(CH_2)_m$ and i is 0 or 1; m=0-12.

In one aspect of the invention, the formula $Z^1$-(PML)-$Z^2$ is represented according to the following:

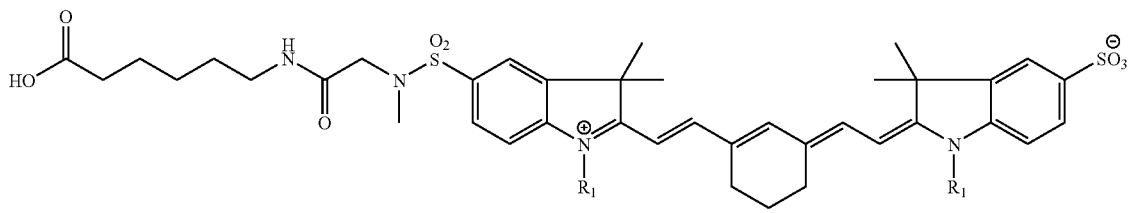

When a compound of the invention is depicted herein by structure indicating the positions of the double bonds in the rings an polymethine linker, it is to be understood that the structure also encompasses any resonance structures as shown, for example, in the figure below

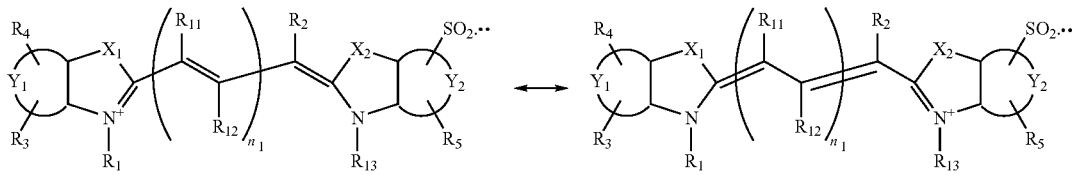

In certain embodiments of the present invention the when $R_6$ is other then hydrogen, unwanted sidechain reactions, are reduced, prevented or inhibited.

In one embodiment, the present invention is directed to compounds representing $Z^1$-(PML)-$Z^2$-BM by the formula:

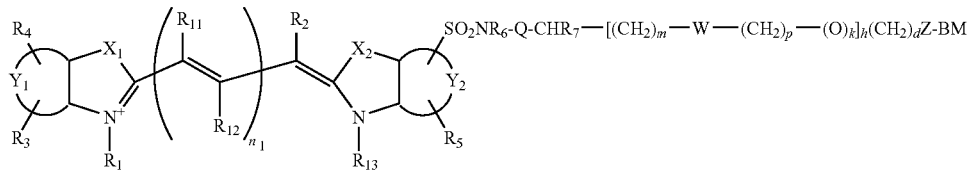

wherein BM is a biomolecule chemically linked to Z to form a biocompatible molecule.

BM is a moiety that changes or alters or enhances accumulation, biodistribution, elimination, targeting, binding, and/or recognition of the fluorochromes of the general structure $Z^1$-(PML)-$Z^2$. BMs include but are not limited to antibodies and fragments thereof, proteins, peptides, amino acids, antibodies (or antigen-binding antibody fragments, such as single chain antibodies), glycoproteins, ligands for cell receptors, polysaccharides, nucleosides, aptamers, cell receptors themselves, enzyme substrates, enzyme cofactors, biotin, hormones, neurohormones, neurotransmitters, growth factors, cytokines, lymphokines, lectins, selecting, toxins, and carbohydrates. Other targeting and delivery approaches using various biomolecules can also be used, such as folate-mediated targeting (Leamon & Low, *Drug Discovery Today*, 6:44-51, 2001), transferrin, vitamins, carbohydrates and ligands that target internalizing receptors, including, but not limited to, asialoglycoprotein receptor, somatostatin, nerve growth factor, oxytocin, bombesin, calcitonin, arginine vasopressin, angiotensin II, atrial natriuretic peptide, insulin, glucagons, prolactin, gonadotropin, various opioids and urokinase-type plasminogen activator. Also included are membrane, transmembrane, and nuclear translocation signal sequences, which can be derived from a number of sources including, without limitation, viruses and bacteria. BM can also be an organic molecule, polymer, dendrimer, drug, lipid, lipid assembly, therapeutic drug molecules, polymeric microparticle, cells, or a nanoparticle. In certain embodiments, BMs can also include small molecule drugs, phototherapeutic molecules and derivatives thereof.

In certain embodiments of the present invention, when BM is chemically linked to a compound of the present invention the fluorescence of the compound of the present invention is enhanced. In certain embodiments the fluorescence is enhanced by about 10%, about 25%, about 50% or more than about 50% which compared with the unlinked compound.

In one aspect of the invention several copies of BM are chemically linked to Z via multivalent linkers or linkers containing several reactive functional groups to form a biocompatible fluorescent molecule of the structure ($Z^1$-(PML)-$Z^2$)-(($L$)$_w$-(BM)q)t, wherein L is a linker or multivalent linker, and t=1-6, w=1-500 and q=1-500. ($L$)$_w$ represents copies of the same linker or a combination of different linkers.

Examples of appropriate linker moieties for compounds of the present invention (carbocyanine dyes) have been previously described in the literature (U.S. Pat. Appl. 2002/0064794 (2002); U.S. Pat. No. 6,086,737 to Patonay et al. (2000); U.S. Pat. No. 6,048,982 to Waggoner (2000); U.S. Pat. No. 6,747,159 to Caputo (2004); U.S. Pat. No. 6,448,008 to Caputo (2002) all incorporated by reference).

In another aspect of the invention, more than one compounds of the present invention (fluorochrome) of the structure $Z^1$-(PML)-$Z^2$ can be chemically linked to a single BM to form a biocompatible fluorescent molecule of the structure [$Z^1$-(PML)-$Z^2$]$_k$-BM, wherein k=1-500.

In one embodiment the compounds (fluorochromes) and biocompatible fluorescent molecules of the present invention have an absorption and emission maxima between about 440 and about 1100 nm, between about 550 and about 800 nm, between about 500 and about 900 nm or between about 600 and about 900 nm.

In one embodiment the compounds (fluorochromes) and biocompatible fluorescent molecules of the present invention are activated after target interaction. "Activated after target interaction" is meant a change that alters a detectable property, e.g., an optical property, of the fluorochromes or biocompatible fluorescent molecules. This includes, but is not limited to, a modification, alteration, or binding (covalent or non-covalent) that results in a detectable difference in properties, e.g., optical properties of the fluorochromes or biocompatible fluorescent molecules, e.g., changes in the fluorescence signal amplitude (e.g., dequenching and quenching), change in wavelength, fluorescence lifetime, spectral properties, or polarity. In another embodiment, a quencher molecule is used to quench the fluorescent signal of the biocompatible fluorescent molecules. By adopting these activated and unactivated states, it is therefore possible to determine whether the fluorochrome or biocompatible fluorescent molecule is active or inactive in a subject by identifying a change in the signal intensity. In addition, the fluorochromes and biocompatible fluorescent molecules can be designed such that the they exhibit little or no signal until activated. Activation can be, without limitation, by enzymatic cleavage, enzymatic conversion, phosphorylation or dephosphorylation, conformation change due to binding, enzyme-mediated splicing, enzyme-mediated transfer, hybridization of complementary DNA or RNA, analyte binding, such as association with an analyte such as $Na^+$, $K^+$, $Ca^{2+}$, $Cl^-$, or another analyte, change in hydrophobicity of the environment and chemical modification.

In one embodiment the compounds (fluorochromes) and biocompatible fluorescent molecules of the present invention have a high binding affinity to a target.

Also provided herein is a method of in vivo optical imaging, the method comprising (a) administering to a subject a compound (fluorochrome) or biocompatible fluorescent molecule of the present invention; (b) allowing time for the compound (fluorochrome) or biocompatible fluorescent molecule to distribute within the subject or to contact or interact with a biological target; (c) illuminating the subject with light of a wavelength absorbable by the compound (fluorochrome) or biocompatible fluorescent molecule; and (d) detecting the optical signal emitted by the compound (fluorochrome) or biocompatible fluorescent molecule.

The optical signal generated by the compound (fluorochromes) or biocompatible fluorescent molecule of the present invention, whether collected by tomographic, reflectance, planar, endoscopic, microscopic, surgical goggles, video imaging technologies, or other methods such as microscopy including intravital and two-photon microscopy, and whether used quantitatively or qualitatively, is also considered to be an aspect of the invention.

One aspect of the invention is a method wherein the presence, absence, distribution, or level of optical signal emitted by the compound (fluorochrome) or biocompatible fluorescent molecule of the present invention is indicative of a disease state.

The invention also features a method of using the compounds (fluorochromes) and biocompatible fluorescent molecules of the present invention to detect an abnormality in a patient or subject, e.g., any abnormality associated with a disease such as cancer, a cardiovascular disease, AIDS, a neurodegenerative disease, an inflammatory disease, a respiratory disease, a metabolic disease, a bone disease or an immunologic disease. The invention also features a method of assessing the effect of a compound or therapy on a specified molecular target by using the compounds (compositions) of the present invention, wherein the subject is imaged prior to and after treatment with the compound or therapy, and the corresponding images are compared.

One aspect of the invention is in the conjugation to drugs, ligands, proteins, peptides, macromolecules, polymers, nanoparticles, or other BMs with multiple reactive groups. Such a conjugation results in a blue shift in the absorbance of the fluorochrome. This provides a mechanism of minimizing background fluorescence during in vivo imaging of activatable but quenched fluorescent probes.

In another aspect, the invention features an in vivo or in vitro optical imaging method comprising (a) administering to a sample or subject a compound of the present invention, for example, a biocompatible N,N-disubstituted sulfonamide fluorochrome containing imaging probes of the present invention; (b) allowing time for the N,N-disubstituted sulfonamide fluorochrome containing imaging probes to distribute within the subject or to contact or interact with a biological target; (c) illuminating the subject with light of a wavelength absorbable by the N,N-disubstituted sulfonamide fluoro chrome containing imaging probes; and (d) detecting the optical signal emitted by the N,N-disubstituted sulfonamide fluorochrome containing imaging probes.

The imaging method steps of the present invention can also be repeated at predetermined intervals thereby allowing for the evaluation of emitted signal of the N,N-disubstituted sulfonamide fluorochrome containing imaging probes in a subject or sample over time. The emitted signal may take the form of an image. The subject may be a vertebrate animal, for example, a mammal, including a human. The animal may also be non-vertebrate, (e.g., *C. elegans, drosophila*, or other model research organisms, etc.). The sample can include, without limitation, cells, cell culture, tissue sections, organs, organ sections, cytospin samples, or the like.

The invention also features an in vivo method for selectively detecting and imaging two or more N,N-disubstituted sulfonamide fluorochrome containing imaging probes simultaneously. The method comprises administering to a subject two or more N,N-disubstituted sulfonamide fluorochrome containing imaging probes, either at the same time or sequentially, whose optical properties are distinguishable. The method therefore allows the recording of multiple events or targets.

The invention also features an in vivo method for selectively detecting and imaging one or more N,N-disubstituted sulfonamide fluorochrome containing imaging probes, simultaneously with one or more targeted or activatable optical imaging probes, or in a dual imaging protocol with magnetic resonance imaging, computed tomography (CT), X-ray, ultrasound, or nuclear medicine imaging modalities and their respective imaging agents. The method comprises administering to a subject one or more imaging probes, either at the same time or sequentially, including at least one N,N-disubstituted sulfonamide fluorochrome containing imaging probe, whose properties are distinguishable from that of the others. In one aspect a dual imaging protocol is optical and magnetic resonance imaging using N,N-disubstituted sulfonamide fluorochrome containing imaging probes sequentially or nearly simultaneously with magnetic resonance imaging agents, (for example, iron oxide based agents or gadolinium based agents such as gadopentetate). The method therefore, allows the recording of multiple events or targets using more than one imaging modality or imaging agent.

In another aspect, the invention features an in vitro optical imaging method comprising contacting the sample with N,N-disubstituted sulfonamide fluorocrome containing imaging probes; allowing time for the probes to become activated or bind to a target of interest in the sample; optionally, removing the unbound probes; illuminating the target with light of a wavelength absorbable by the N,N-disubstituted sulfonamide fluorochrome containing imaging probes; and detecting the optical signal emitted by the N,N-disubstituted sulfonamide fluorochrome containing imaging probes.

After administration, detection can occur, for example, by in vitro methods, i.e., flow cytometry or by in vivo imaging methods, i.e., tomographic, catheter, planar/reflectance systems or endoscopic systems.

In one embodiment, the N,N-disubstituted sulfonamide fluorochrome (or imaging probes derived thereof) can be used to label a sample ex vivo. The sample, e.g., cells, can be derived directly from a subject or from another source (e.g., from another subject, cell culture etc.). The N,N-disubstituted sulfonamide fluorochrome containing imaging probe can be mixed with the cells to effectively label the cells (covalently or non-covalently) and the resulting labeled cells injected into a subject. This method can be used for monitoring trafficking and localization of certain cell types, including T-cells, tumor cells, immune cells, stem cells, and other cell types. In particular, this method may be used to monitor cell based therapies. The sample can also be derived from non-mammalian sources including but not limited to plants, insects, viruses, bacteria, and bacteriophage.

Another aspect of the invention features N,N-disubstituted sulfonamide fluorochrome containing imaging probes that can be used for in vivo imaging and labeling samples ex vivo, including cells, without the use of dimethylsulfoxide (DMSO) or other organic solvents (i.e. physiologic buffers or solutions) that are generally toxic to biological subjects or samples.

For labeling of BMs or cells, the compounds (fluorochromes) of the present invention can be incubated with BMs at various concentrations for about 5 minutes to 24 hours or more at about 4°-37° C. After the incubation the free or fluorochrome that has not been chemically linked to the BM can be removed, such as by chromatography or ultrafiltration methods that are well known in the art. For cells, after the incubation, the cells can be centrifuged to create a cell pellet from which the supernatant is removed. Cells can be resuspended in culture media or physiologic saline to wash away residual, unbound or free fluorochrome. This can be repeated several times. In this manner, cells can be labeled either by direct conjugation to internal or external cellular molecules or by non-specific cell uptake into various intracellular compartments, including but not limited to cytosol, endosomes, nucleus, golgi apparatus, and other intracellular organelles.

Another aspect of the invention features N,N-disubstituted sulfonamide fluorochrome containing imaging probes formulated in a pharmaceutical composition suitable for administration to animal, including human, subjects. The pharmaceutical composition can include the nanoparticles and one or more stabilizers in a physiologically relevant carrier.

Another aspect of the invention features biocompatible fluorescent N,N-disubstituted sulfonamide fluorochromes and N,N-disubstituted sulfonamide fluorochrome containing imaging probes formulated in pharmaceutical compositions suitable for administration to animal, including human, subjects and cells. The pharmaceutical composition can include one or more stabilizers in a physiologically relevant carrier.

Suitable example of stabilizers for use in the methods of the present invention include but are not limited to low molecular weight carbohydrate, in one aspect it is a linear polyalcohol, such as sorbitol, and glycerol; or mannitol.

Other low molecular weight carbohydrates, such as inositol, may also be used. Physiologically relevant carriers can include water, saline, and may further include agents such as buffers, and other agents such as preservatives that are compatible for use in pharmaceutical formulations.

The invention also features a method of gene sequence recognition using fluorescent N,N-disubstituted sulfonamide fluorochromes, labeled nucleic acid recognition molecules, including DNA, RNA, modified nucleic acid, PNA, molecular beacons, aptamers, or other nucleic acid binding molecules (for example, small interfering RNA or siRNA). The method includes the use of one or more fluorescent N,N-disubstituted sulfonamide fluorochromes, together with techniques such as hybridization, ligation, cleavage, recombination, synthesis, sequencing, mutation detection, real-time polymerase chain reactions, in situ hybridization, and the use of microarrays. For example, for detecting a single stranded nucleic acid (i.e., mRNA, cDNA or denatured double-stranded DNA) in a sample, via nucleic acid hybridization principles, a fluorescent N,N-disubstituted sulfonamide fluorochrome chemically linked to a single-stranded nucleic acid is contacted with a sample containing one or more single stranded nucleic acids and the fluorescence of the fluorescent N,N-disubstituted sulfonamide fluorochrome is detected, wherein the presence or level of fluorescence signal emitted by the fluorescent N,N-disubstituted sulfonamide fluorochrome indicates the presence or amount of nucleic acid in the sample.

The optical signal generated by the N,N-disubstituted sulfonamide fluorochromes or N,N-disubstituted sulfonamide fluorochrome containing imaging probes, or derivatives thereof, whether collected by tomographic, reflectance, planar, endoscopic, microscopic, surgical goggles or imager, video imaging technologies, or other methods such as microscopy including intravital and two-photon microscopy, and whether used quantitatively or qualitatively, is also considered to be an aspect of the invention.

Another aspect of the invention features a kit, which includes the N,N-disubstituted sulfonamide fluorochromes or N,N-disubstituted sulfonamide fluorochrome containing imaging probes, and optionally, and instructions for using the fluorochromes or imaging probes for in vivo or in vitro imaging methods. The kit optionally may include components that aid in the use of the fluorochromes or imaging probes for the disclosed methods, such as buffers, and other formulating agents; alternatively, the kit may include medical devices that aid in the administration of the imaging probes to subjects.

The N,N-disubstituted sulfonamide fluorochromes or N,N-disubstituted sulfonamide fluorochrome containing imaging probes, and pharmaceutical compositions of the present invention can be administered orally, parentally, by inhalation, topically, rectally, nasally, buccally, vaginally, or via an implanted reservoir. The term "parental administration" includes intravenous, intramuscular, subcutaneous, intraarterial, intraarticular, intrasynovial, intrasternal, intrathecal, intraperitoneal, intracisternal, intrahepatic, intralesional, intracranial and intralymphatic injection or infusion techniques. The N,N-disubstituted sulfonamide fluorochromes or N,N-disubstituted sulfonamide fluorochrome can also be administered via catheters or through a needle to a tissue.

In one embodiment, an effective amount (which is an amount effective to cause or increase fluorescence) of the compounds of the present invention are administered. In one embodiment, between about 1 ng/kg and about 100 mg/kg, between about 100 ng/kg and 10 mg/kg, between about 1 µg/kg and about 5 mg/kg, between about 10 µg/kg and about 2 mg/kg, between about 50 µg/kg and about 1 mg/kg of the compound of the present invention is administered.

Preferred N,N-disubstituted sulfonamide fluorochromes or N,N-disubstituted sulfonamide fluorochrome containing imaging probes have the following properties: (1) high quantum yield (e.g., quantum yield greater than 5% in aqueous medium), (2) narrow emission spectrum (e.g., less than 75 nm; more preferably less than 50 nm), (3) spectrally separated absorption and emission spectra (e.g., separated by more than 20 nm; more preferably by more than 50 nm), (3) have high chemical stability and photostability (e.g., retain fluorescent properties after exposure to light), (4) are non toxic or minimally toxic to cells or subjects at doses used for imaging protocols, (as measured for example, by $LD_{50}$ or irritation studies, or other similar methods known in the art) and/or (5) have commercial viability and scalable production for large quantities (e.g., gram and kilogram quantities).

The compounds of the present invention can have one or more sufficiently acidic proton that can react with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

The compounds of the present invention having a sufficiently basic group, such as an amine can react with an organic or inorganic acid to form an acid addition salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

The term "alkyl" as used herein means a saturated straight-chain, branched or cyclic hydrocarbon. When straight-chained or branched, an alkyl group is typically C1-C20, more typically C1-C10; when cyclic, an alkyl group is typically C3-C12, more typically C3-C7. Examples of alkyl groups include methyl, ethyl, n-propyl, iso-propyl, n-butyl, sec-butyl and tert-butyl and 1,1-dimethylhexyl.

An "aliphatic group" is non-aromatic, and may optionally contain one or more units of unsaturation, e.g., double and/or triple bonds. An aliphatic group may be straight-chained or branched and typically contains between 1 and 12 carbon atoms, more typically between 1 and 6 carbon atoms, and even more typically between 1 and 4 carbon atoms. One or more methylene group in an aliphatic group can optionally be replaced by O, S, or NH.

As used herein the term non-aromatic carbocyclic ring or non-aromatic heterocyclic ring as used alone or as part of a larger moiety refers to a non-aromatic carbon or heteroatom containing ring which can be saturated or contain one or more units of unsaturation, having three to fourteen atoms including monocyclic and polycyclic rings in which the carbocyclic or heterocyclic ring can be fused to one or more non-aromatic carbocyclic or heterocyclic rings or one or more aromatic (carbocyclic or heterocyclic) rings.

The term "alkoxy" as used herein is represented by —OR, wherein R is an alkyl group as defined above.

The term "carbonyl" as used herein is represented by —C(=O)R, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or contain one or more units of unsaturation. Examples of heterocyclic groups include piperidinyl, piperizinyl, pyrrolidinyl, pyrazolidinyl, imidazolidinyl, tetrahydroquinolinyl, inodolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below. Preferably the nitrogen is unsubstituted.

A substituted aryl group as defined herein contains one or more substitutable ring atoms, such as carbon or nitrogen ring atoms. Examples of suitable substituents on a substitutable ring carbon atom of an aryl or aliphatic group include halogen (e.g., —Br, Cl, I and F), —OH, C1-C4 alkyl, C1-C4 haloalkyl, —NO$_2$, C1-C4 alkoxy, C1-C4 haloalkoxy, —CN, —NH$_2$, C1-C4 alkylamino, C1-C4 dialkylamino, —C(O)NH$_2$, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)$_2$, —NHC(O)O—(C1-C4 alkyl), —C(O)OH, —C(O)O—(C1-C4 alkyl), —NHC(O)NH$_2$, —NHC(O)NH(C1-C4 alkyl), —NHC(O)N(C1-C4 alkyl)$_2$, —NH—C(=NH)NH$_2$, —SO$_2$NH$_2$—SO$_2$NH(C1-C3 alkyl), —SO$_2$N(C1-C3alkyl)$_2$, NHSO$_2$H, NHSO$_2$(C1-C4 alkyl) and aryl. Preferred substituents on aryl groups are as defined throughout the specification.

Examples of suitable substituents on a substitutable ring nitrogen atom of an aryl group include C1-C4 alkyl, NH$_2$, C1-C$_4$ alkylamino, C1-C4 dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3alkyl), —SO$_2$N(C1-C3alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, Substituted alkyl, aliphatic, non-aromatic carbocyclic or heterocyclic group as defined herein contain one or more substituents. Examples of suitable substituents for an alkyl group include those listed above for a substitutable carbon of an aryl and aliphatic and the following: =O, =S, =NNHR, =NN(R)$_2$, =NNHC(O)R, —NNHCO$_2$ (alkyl), =NNHSO$_2$ (alkyl), =NR, spiro cycloalkyl group or fused cycloalkyl group. R** in each occurrence, independently is —H or C1-C6 alkyl. Preferred substituents on alkyl aliphatic, non-aromatic carbocyclic or heterocyclic group groups are as defined throughout the specification.

In vitro Testing and Use

The fluorochromes and biocompatible fluorescent molecules of the present invention can be tested in vitro by one skilled in the art to assess its biological and performance characteristics. For instance, different types of cells grown in culture can be used to assess their biological and performance characteristics. Uptake, labeling, binding targeting or cellular localization of the fluorochromes and biocompatible fluorescent molecules can be assessed using techniques known in the art such as spectroscopy methods, fluorescent microscopy, and flow cytometry. For example, the fluorochromes and biocompatible fluorescent molecules of the present invention can be contacted with a sample for a period of time and then washed to remove any free or unbound molecules. The sample can then be viewed using a fluorescent microscope equipped with appropriate filters matched to the optical properties of the fluorochromes and biocompatible fluorescent molecules of the present invention. Fluorescent microscopy of cells in culture is also a convenient means for determining whether uptake and binding occurs in one or more subcellular compartments. Tissues, tissue sections and other types of samples such as cytospin samples can also be used in a similar manner to assess the biological and performance characteristics of the molecules. Other fluorescent detection methods including, but not limited to flow cytometry, immunoassays, hybridization assays, and microarray analysis can also be used.

Optical Imaging

The general principles of fluorescence, optical image acquisition, and image processing can be applied in the practice of the invention. For a review of optical imaging techniques, see, e.g., Alfano et al., *Ann. NY Acad. Sci.* 820:248-270, 1997.

An imaging system useful in the practice of this invention typically includes three basic components: (1) an appropriate light source for fluorochrome and biocompatible fluorescent molecule excitation, (2) a means for separating or distinguishing emissions from light used for the excitation, and (3) a detection system to detect the optical signal emitted.

In general, the optical detection system can be viewed as including a optical gathering/image forming component and a optical detection/image recording component. Although the optical detection system can be a single integrated device that incorporates both components, the optical gathering/image forming component and light detection/image recording component will be discussed separately.

A particularly useful optical gathering/image forming component is an endoscope. Endoscopic devices and techniques which have been used for in vivo optical imaging of numerous tissues and organs, including peritoneum (Gahlen et al., *J. Photochem. Photobiol. B* 52:131-135, 1999), ovarian cancer (Major et al., *Gynecol. Oncol.* 66:122-132, 1997), colon and rectum (Mycek et al., *Gastiointest. Endosc.* 48:390-394, 1998; and Stepp et al., *Endoscopy* 30:379-386, 1998), bile ducts (Izuishi et al., *Hepatogastroenterology* 46:804-807, 1999), stomach (Abe et al., *Endoscopy* 32:281-286, 2000), bladder (Kriegmair et al., *Urol. Int.* 63:27-31, 1999; and Riedl et al., *J. Endourol.* 13:755-759, 1999), lung (Hirsch et al., *Clin Cancer Res* 7:5-220, 2001), brain (Ward, *J. Laser Appl.* 10:224-228, 1998), esophagus, and head and neck regions can be employed in the practice of the present invention.

Other types of optical gathering components useful in the invention are catheter-based devices, including fiber optics devices. Such devices are particularly suitable for intravascular imaging. See, e.g., Tearney et al., *Science* 276:2037-2039, 1997; and *Circulation* 94:3013, 1996.

Still other imaging technologies, including phased array technology (Boas et al., *Proc. Natl. Acad. Sci. USA* 91:4887-4891, 1994; Chance, *Ann. NY Acad. Sci.* 838:29-45, 1998), optical tomography (Cheng et al., *Optics Express* 3:118-123, 1998; and Siegel et al., *Optics Express* 4:287-298, 1999), intravital microscopy (Dellian et al., *Br. J. Cancer* 82:1513-1518, 2000; Monsky et al, *Cancer Res.* 59:4129-4135, 1999; and Fukumura et al., *Cell* 94:715-725, 1998), confocal imaging (Korlach et al., *Proc. Natl. Acad. Sci. USA* 96:8461-8466, 1999; Rajadhyaksha et al., *J. Invest. Dermatol.* 104:946-952, 1995; and Gonzalez et al., *J. Med.* 30:337-356, 1999) and fluorescence molecular tomography (FMT) (Nziachristos et al., *Nature Medicine* 8:757-760, 2002; U.S. Pat. No. 6,615,063, PCT Application No. WO 03/102558, and PCT US/03/07579) can be employed in the practice of the present invention, the IVIS® Imaging System (Xenogen, Alameda, Calif.), Maestro (CRI, Woburn, Mass.) the SoftScan® and the eXplore Optix™ (Advanced Research Technologies, Montreal, Canada) system can be employed in the practice of the present invention.

A suitable optical detection/image recording component, e.g., charge coupled device (CCD) systems or photographic film, can be used in the invention. The choice of optical detection/image recording will depend on factors including type of optical gathering/image forming component being used. Selecting suitable components, assembling them into an optical imaging system, and operating the system is within ordinary skill in the art.

Diagnostic and Disease Applications and Methods

The methods of the invention can be used to determine a number of indicia, including tracking the localization of the fluorochromes and biocompatible fluorescent molecules in the subject over time or assessing changes or alterations in the metabolism and/or excretion of the molecules in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The invention can be used to help a physician or surgeon to identify and characterize areas of disease, such as arthritis, cancers and specifically colon polyps, or vulnerable plaque, to distinguish diseased and normal tissue, such as detecting tumor margins that are difficult to detect using an ordinary operating microscope, e.g., in brain surgery, help dictate a therapeutic or surgical intervention, e.g., by determining whether a lesion is cancerous and should be removed or non-cancerous and left alone, or in surgically staging a disease, e.g., intraoperative lymph node staging, sentinel lymph node mapping, or assessing intraoperative bleeding.

The methods of the invention can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring drug therapy, including cell based therapies. The methods of the invention can also be used in prognosis of a disease or disease condition. Examples of such disease or disease conditions include inflammation (e.g., inflammation caused by arthritis, for example, rheumatoid arthritis), cancer (e.g., colorectal, ovarian, lung, breast, prostate, cervical, skin, brain, gastrointestinal, mouth, esophageal, bone), cardiovascular disease (e.g., atherosclerosis and inflammatory conditions of blood vessels, ischemia, stroke, thrombosis), dermatologic disease (e.g., Kaposi's Sarcoma, psoriasis), ophthalmic disease (e.g., macular degeneration, diabetic retinopathy), infectious disease (e.g., bacterial, viral, fungal and parasitic infections, including Acquired Immunodeficiency Syndrome), immunologic disease (e.g., an autoimmune disorder, lymphoma, multiple sclerosis, rheumatoid arthritis, diabetes mellitus), central nervous system disease (e.g., a neurodegenerative disease, such as Parkinson's disease or Alzheimer's disease), inherited diseases, metabolic diseases, environmental diseases (e.g., lead, mercury and radioactive poisoning, skin cancer), and bone-related disease (e.g., osteoporosis, primary and metastatic bone tumors, osteoarritis). The methods of the invention can therefore be used, for example, to determine the presence of tumor cells and localization of tumor cells, the presence and localization of inflammation, including the presence of activated macrophages, for instance in atherosclerosis or arthritis, the presence and localization of vascular disease including areas at risk for acute occlusion (i.e., vulnerable plaques) in coronary and peripheral arteries, regions of expanding aneurysms, unstable plaque in carotid arteries, and ischemic areas. The methods and compounds (compositions) of the invention can also be used in identification and evaluation of apoptosis, necrosis, hypoxia and angiogenesis.

Optical imaging modalities and measurement techniques include, but are not limited to, fluorescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; intravital imaging; two photon imaging; interferometry; coherence interferometry; diffuse optical tomography and fluorescence molecular tomography, and measurement of light scattering, absorption, polarisation, luminescence, fluorescence lifetime, quantum yield, and quenching.

The compounds (compositions) and methods of the present invention can be used in combination with other imaging compositions and methods. For example, the methods of the present invention can be used in combination with other traditional imaging modalities such as X-ray, computed tomography (CT), positron emission tomography (PET), single photon computerized tomography (SPECT), and magnetic resonance imaging (MRI). For instance, the compounds (compositions) and methods of the present invention can be used in combination with CT and MR imaging to obtain both anatomical and biological information simultaneously, for example, by co-registration of a tomographic image with an image generated by another imaging modality. In particular, the combination with MRI or CT is preferable, given the high spatial resolution of these imaging techniques. The compounds (compositions) and methods of the present invention can also be used in combination with X-ray, CT, PET, SPECT and MR contrast agents or the fluorescent silicon nanoparticle imaging probes of the present invention may also contain components, such as iodine, gadolinium atoms and radioactive isotopes, which can be detected using CT, PET, SPECT, and MR imaging modalities in combination with optical imaging.

Kits

The compounds (compositions) described herein can be packaged as a kit, which may optionally include instructions for using the fluorochromes or biocompatible fluorescent molecules in various exemplary applications. Non-limiting examples include kits that contain, e.g., the compounds (compositions) in a powder or lyophilized form, and instructions for using, including reconstituting, dosage information, and storage information for in vivo and/or in vitro applications. Kits may optionally contain containers of the compounds (compositions) in a liquid form ready for use, or requiring further mixing with solutions for administration. For in vivo applications, the kit may contain the compounds (compositions) in a dosage and form suitable for a particular application, e.g. a liquid in a vial, a topical creams, etc.

The kit can include optional components that aid in the administration of the unit dose to subjects, such as vials for reconstituting powder forms, syringes for injection, customized IV delivery systems, inhalers, etc. The kits may be supplied in either a container which is provided with a seal which is suitable for single or multiple puncturing with a hypodermic needle (e.g. a crimped-on septum seal closure) while maintaining sterile integrity. Such containers may contain single or multiple subject doses. Additionally, the unit dose kit can contain customized components that aid in the detection of the compounds (compositions) in vivo or in vitro, e.g., specialized endoscopes, light filters. The kits may also contain instructions for preparation and administration of the compounds (compositions). The kit may be manufactured as a single use unit dose for one subject, multiple uses for a particular subject; or the kit may contain multiple doses suitable for administration to multiple subjects ("bulk packaging"). The kit components may be assembled in cartons, blister packs, bottles, tubes, and the like.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

In certain embodiments of the present invention the compounds of the present invention are not:

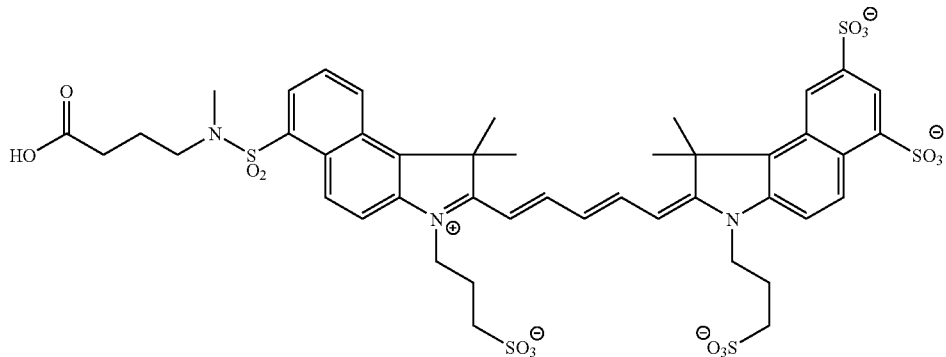

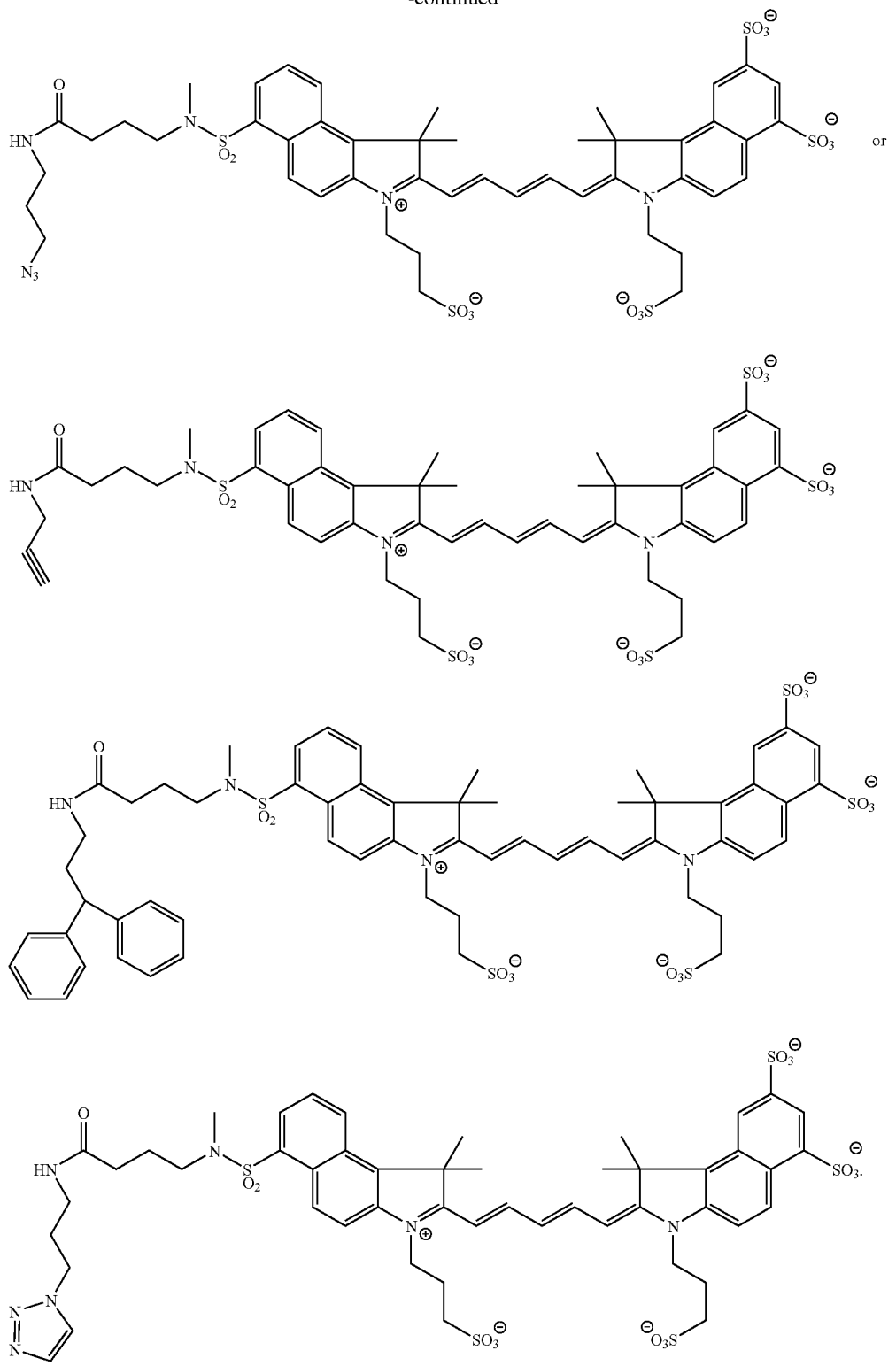

EXAMPLES

The following non limiting examples demonstrate the synthesis of N,N-disubstituted sulfonamide fluorochromes. Representative materials and methods that may be used in preparing the compounds of the invention are described further below. All chemicals and solvents (reagent grade) were used as supplied commercially generally without further purification.

The analytical and preparative HPLC methods generally utilized are:

A Column: Agilent Zorbax 80 Å, Extend C18, 4.6×250 mm (5 μm).
  Mobile phase: Acetonitrile, 25 mM triethylammonium acetate.
B Column: Varian Dynamax, 100 Å, C18, 41.4×250 mm.
  Mobile phase: Acetonitrile, 25 mM triethylammonium acetate.
C Column: Phenomenex Jupiter, 300 Å, C18
  Mobile phase: Acetonitrile, 25 mM triethylammonium acetate.

Example 1

Synthesis of Example 1

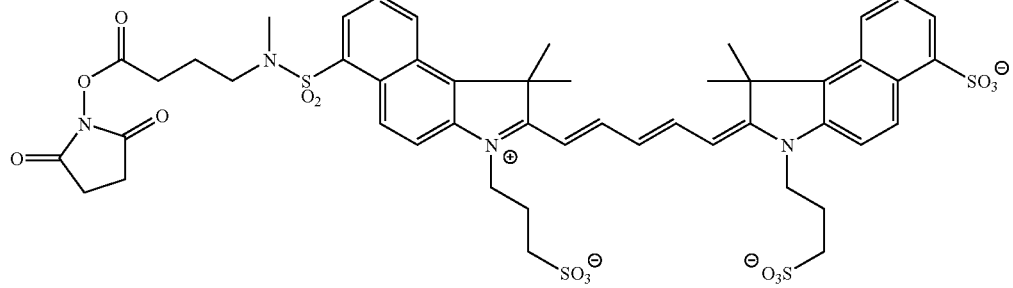

Compound A

Part A. Preparation of 6-hydrazino-1-naphthalene Sulfonate I

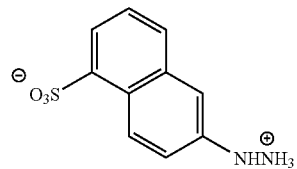

6-Amino-1-naphthalenesulfonate (10 g, 45 mmol) (TCI), sodium hydroxide (1.8 g, 45 mmol) (Mallinckrodt) and sodium nitrite (3.7 g, 54 mmol) (Aldrich) were combined in 50 mL water and stirred to obtain a clear, brown solution. The solution was cooled to 0° C. and added drop wise over 15 minutes to 50 mL of concentrated hydrochloric acid and 30 g of ice cooled in an ice/salt bath to <0° C. Stannous chloride (18.7 g, 99 mmol, Aldrich) was dissolved in 50 mL 6M hydrochloric acid, cooled to 0° C. and added to the reaction mixture drop wise over 15 min. with stirring. The resulting suspension was allowed to stir at 0° C. for 1 h. The yellow precipitate was filtered off and washed with distilled water, methanol, isopropanol and finally ether to yield 9 g of the desired hydrazine (84%).

Part B. Preparation of 2,3,3-trimethylbenzindole-7-sulfonate II

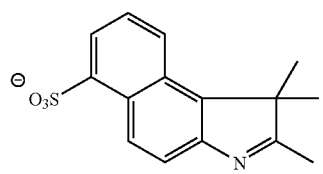

6-Hydrazino-1-naphthalene sulfonate (5 g, 21 mmol), isopropyl methyl ketone (8.1 g, 93 mmol, Aldrich) and potassium acetate (6 g, 61 mmol) were combined in 70 mL glacial acetic acid in a 100 mL pressure vessel with a stir bar. The vessel was sealed and heated to 145° C. for 22 hours. The slurry was poured into ether and the precipitate was dissolved in ethanol with the aid of heat and sonication and then filtered. The filtrate was evaporated to give the title compound as a yellow hygroscopic solid.

Part C. Preparation of Ethyl-4-(methylamino)butyrate Hydrochloride III

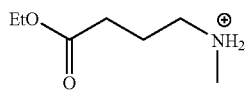

4-(Methylamino)butyric acid hydrochloride (7.5 g, 49 mmol, Aldrich) was dissolved in 75 mL of absolute ethanol and 4 mL of 2.0 M HCl in ether (Aldrich) was added. The solution, which became clear upon heating to 70° C., was refluxed for 20 hours. The solvent was removed in vacuo resulting in a white, solid, hydrochloride salt in quantitative yield. $^1$HNMR (300 MHz, CDCl$_3$) δ 1.20 (t, J=7.2 Hz, 3H), 2.13 (m, 2H), 2.47 (t, J=7.2 Hz, 2H), 2.67 (t, J=5.7 Hz, 3H), 3.00 (broad m, 2H), 4.07 (q, J=7.2 Hz, 2H), 9.50 (broad s, 2H).

Part D. Preparation of 2,3,3-trimethylbenzindole-6-[N-methyl-N-(ethyl-4-butyrato)]sulfonamide IV

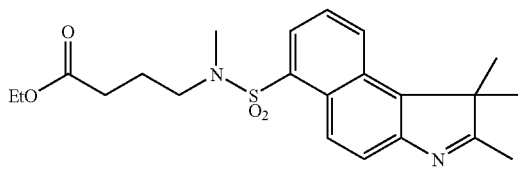 [SMILES: CCOC(=O)CCCN(C)S(=O)(=O)c1cccc2c3c(ccc12)N=C(C)C3(C)C]

2,3,3-Trimethylbenzindole-6-sulfonic acid potassium salt (3 g, 9.2 mmol) was placed in 50 mL of dry acetonitrile. Phosphorous pentachloride (4 g, 19 mmol, Aldrich) was added slowly, and the mixture was refluxed for 1 hour resulting in a red solution with off-white solid. The red solution was filtered and the solvent reduced to 10 mL by evaporation under reduced pressure. The solution was poured into 200 mL of ether and the red solid precipitate was collected by filtration. The solid was redissolved in acetonitrile and ethyl-4-(methylamino)butyrate hydrochloride (2 g, 11 mmol) was added followed by triethylamine (1.1 g, 11 mmol). The solution was filtered, evaporated to dryness and purified by flash chromatography on silica gel 60 eluting with dichloromethane containing 0.5% triethylamine.

Part E. Preparation of 2,3,3-trimethyl-1-(sulfonatopropyl)-benzindolinium-6-[N-methyl-N-(ethyl-4-butyrato)]sulfonamide V

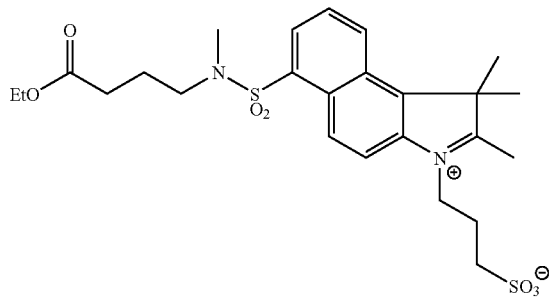

2,3,3-Trimethyl-6-[N-methyl-N-(ethyl-4-butyrato)]sulfonamide (250 mg, 0.6 mmol) and 1,3-propanesultone (140 mg, 1.15 mmol, Aldrich) were dissolved in 2 mL of o-dichlorobenzene. The solution was heated in a sealed tube at 120° C. for 16 hours. The solution was allowed to cool to room temperature, and then 40 mL of ether was added. The purple solid was filtered and rinsed with three portions of 25 mL of ether and dried in vacuum. 260 mg of a dark purple, hygroscopic powder were obtained (80%). MALDI-TOF-MS m/e 539.19 [M]+ calculated for $C_{25}H_{35}N_2O_7S_2^+$, found 539.19.

Part F. Preparation of 6-hydrazino-1,3-naphthalene Disulfonate VI

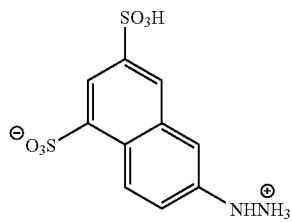

6-Amino-1,3-naphthalene disulfonate disodium salt (10 g, 29 mmol) (TCI) was dissolved in 30 mL of water and added to 50 mL of water and 15 mL of concentrated hydrochloric acid. The slurry was cooled to <0° C. in an ice/acetone bath and sodium nitrite (2.2 g, 32 mmol, Aldrich) was added in 40 mL of cold water drop-wise over 10 minutes. Stannous chloride (11 g, 58 mmol) (Aldrich) was dissolved in 30 mL water and 6 mL concentrated hydrochloric acid, cooled to 0° C. and added to the reaction mixture over 10 minutes. The resulting solution was stirred and allowed to warm to room temperature over 3 hours resulting in a clear, brown solution. The solution was reduced in volume by rotary evaporation and the product precipitated by the addition of isopropanol. Product was filtered, washed with isopropanol and dried in vacuum.

Part G. Preparation of 2,3,3-trimethylbenzindole-5,7-disulfonate VII

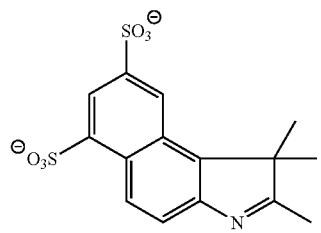

6-Hydrazino-1,3-naphthalene disulfonate (10 g, 25 mmol), isopropyl methyl ketone (12 g, 140 mmol, Aldrich) and potassium acetate (6 g, 61 mmol) were combined in 75 mL glacial acetic acid in a 100 mL pressure vessel with a stir bar. The vessel was sealed and heated to 145° C. for 22 hours. The solution was cooled and the acetic acid was removed by rotary evaporation. The residue was dissolved in methanol and filtered. The product was then precipitated from the methanol filtrate with isopropanol and filtered, washed with isopropanol and ether and dried in vacuum.

Part H. Preparation of 2,3,3-trimethyl-1-(3-sulfonatopropyl)benzindolinium-5,7-disulfonate VIII

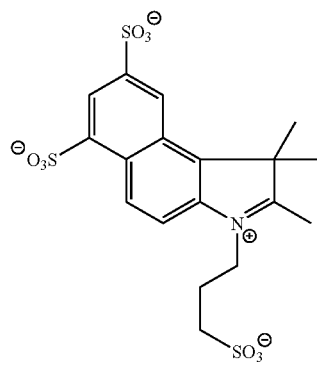

2,3,3-Trimethylbenzindole-6,8-disulfonate (2.2 g, 5 mmol) was dissolved in 50 mL of dry DMF resulting in a clear orange solution. 1,3-Propanesultone (2.8 g, 23 mmol, Aldrich) was added and the solution was heated to 145° C. in a sealed tube for 15 hours, turning dark purple in color. The solution was cooled and poured into 150 mL 2-propanol. The mixture was centrifuged and the supernatant solution decanted off. The solid product was washed on a filter with three 50 mL portions of 2-propanol followed by 50 mL of ether and dried in vacuum, resulting in 2.5 g of a dark purple solid (90%). MALDI-TOF-MS m/e 492.05 [M]+ calculated for $C_{18}H_{22}NO_9S_3^+$, found 492.05.

Part I Preparation of Compound IX

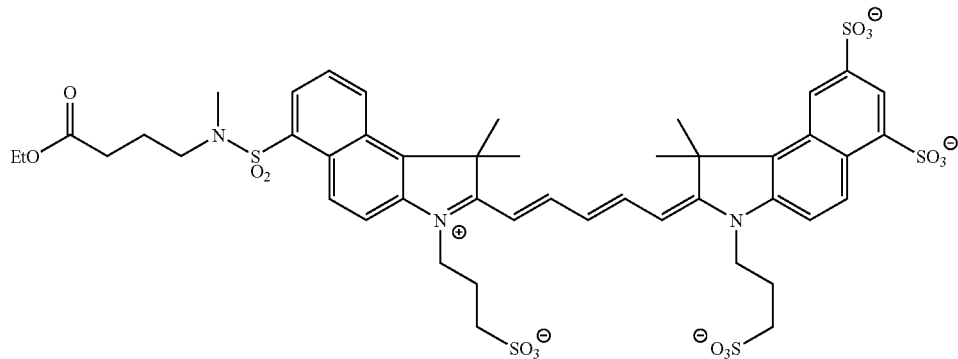

Trisulfonated benzindolinium VIII (250 mg, 0.44 mmol) was dissolved in 5 mL glacial acetic acid and 2 mL acetic anhydride. Malonaldehyde dianiline hydrochloride (112 mg, 0.43 mmol) (TCI) was added and the solution was heated to 120° C. in a sealed tube for 2 h. The solution was cooled and 25 mL of ethyl acetate was added to precipitate the product. The mixture was centrifuged and the ethyl acetate decanted off and the solid was washed with 25 mL of ethyl acetate. The solid was dissolved in 6 mL glacial acetic acid and 2 mL acetic anhydride. Sulfonamide benzindolinium V (235 mg, 0.44 mmol) was added along with 300 mg of potassium acetate and the solution was heated to 125° C. in a sealed tube for 18 hours. The solution was cooled, and 25 mL of ethyl acetate was added to precipitate the product. The mixture was centrifuged and the ethyl acetate decanted off and the solid was washed with 25 mL of ethyl acetate followed by 25 mL of acetonitrile. The product was purified by HPLC yielding 67 mg of pure ethyl ester dye (13%). MALDI-TOF-MS m/e 1066.23 [M]+ calculated for $C_{46}H_{56}N_3O_{16}S_5^+$, found 1066.18. $\lambda_{max}$ (H$_2$O)=673 nm.

Part J. Preparation of Compound X

Compound IX (65 mg, 0.048 mmol) was dissolved in 5 mL of 0.4 M NaOH and stirred at 20° C. for 1 hour resulting in quantitative conversion to the free acid by HPLC. The solution was acidified to pH~3 with 1 M HCl, desalted and lyophilized to give the desired product X. MALDI-TOF-MS m/e 1038.20 [M]+ calculated for $C_{44}H_{52}N_3O_{16}S_5^+$, found 1038.21. $\lambda_{max}$ (H$_2$O)=673 nm.

Part K. Preparation of Example 1

Compound X (21 mg, 0.019 mmol) was dissolved in 1.5 mL dry DMF. Disuccinimidyl carbonate (37 mg, 0.14 mmol) (Aldrich) was added along with 4-dimethylaminopyridine (2.5 mg, 0.02 mmol) (Aldrich). The solution was heated with stirring to 60-65° C. for 1 hour. The active ester was precipitated with 20 mL of ethyl acetate and separated by centrifugation. The dark blue solid was washed with four 20 mL portions of ethyl acetate and dried under vacuum to give the title compound (Compound A). MALDI-TOF-MS m/e 1135.21 [M]+ calculated for $C_{48}H_{55}N_4O_{18}S_5^+$, found 1135.19. $\lambda_{max}$(H$_2$O)=673 nm.

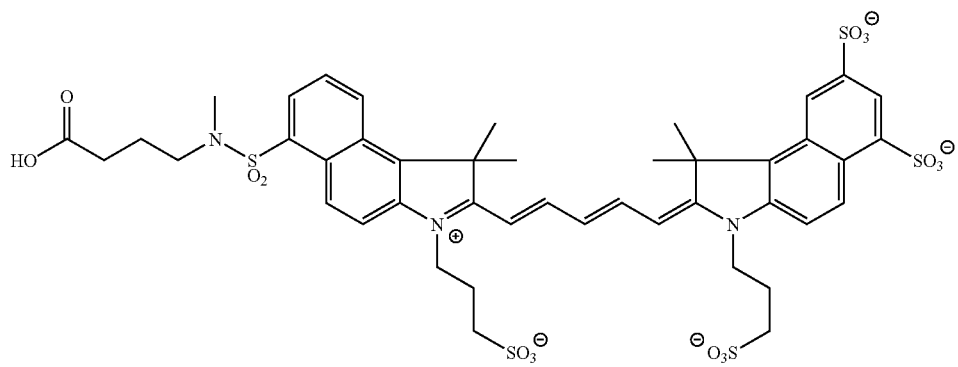

Example 2

Synthesis of Example 2

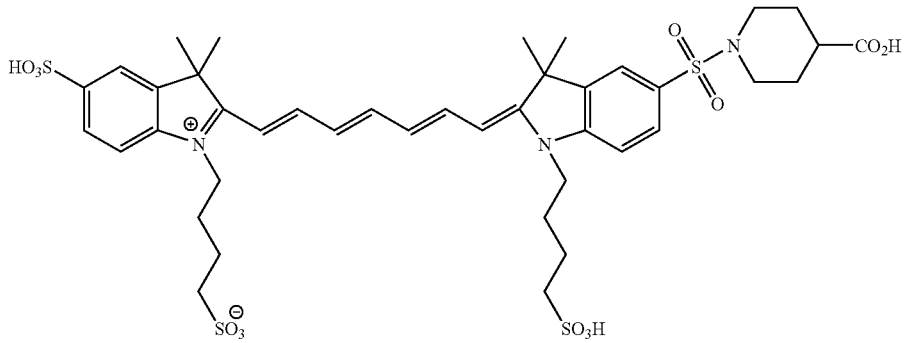

Part A. Preparation of 2,3,3-trimethyl Indolinine 5-sulfonyl Chloride (XI)

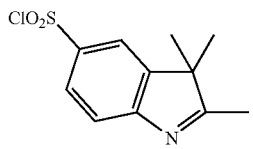

Commercially available 5-sulfo-2,3,3-trimethyl indolinine K salt (5.45 g, 19.6 mmol) was added to a mixture of phosphorous pentachloride ($PCl_5$, 6.12 g, 29.42 mmol, 1.5 equivalent), and $POCl_3$ (3 mL) in a round bottom flask fitted with an air condenser under nitrogen atmosphere, and stirred vigorously for 45 min at 120° C. The contents were cooled to room temperature, dichloromethane added and the sulfonyl chloride was precipitated with 25% hexane in ether, and filtered under nitrogen atmosphere. Repeated for second time and washed with 10% ethyl acetate in hexane. Solid material transferred to an RBF and dried under vacuum for 30 min and the resulting powder (XI) was used immediately for further reaction (3.2 g, 53% yield).

Part B. Preparation of Compound XII

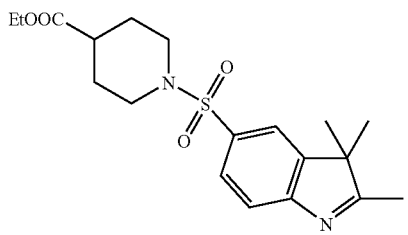 [SMILES: CCOC(=O)C1CCN(S(=O)(=O)c2ccc3c(c2)C(C)(C)C(C)=N3)CC1]

2.22 g of the sulfonyl chloride XI was dissolved in 25 mL acetonitrile and cooled down to 0° C. 1.35 g of ethyl isonipecotate (8.6 mmol) dissolved in 5 mL acetonitrile and 3 mL triethylamine was added in drops over 2 min. Dark brown solution turned yellow first and then orange. After 30 min. stirring at 0° C., reaction mixture was allowed to warm up to room temp. Completion of the reaction was observed by TLC (silica gel, 5% acetonitrile in dichloromethane). Solvents were removed by rotovap. Concentrated crude material was chromatographed over silica gel and purified using acetonitrile-methylene chloride mixture, (10% to 50% gradient). A yield of 1.2 g of yellow dry solid material (XII) was realized at 43%. IR (1728 $cm^{-1}$ for ester).

Part C. Preparation of Compound XIII

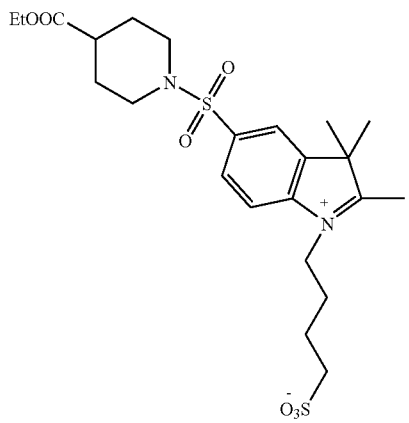

The sulfonamide XII, 1.2 g (MW 395.2, 3.06 mmol) from above was reacted with 2 mL of 1,4-butane sultone (20 mmol) in 20 mL of 1,2-dichlorobenzene and heated at 125° C. for an overnight (16 h). Precipitation of the viscous solution with ether, and washings with hexane with 10% ethyl acetate afforded 300 mg of desired quaternary salt XIII as a dark brown powder (yield 20%).

Part D, Preparation of Compound XIV

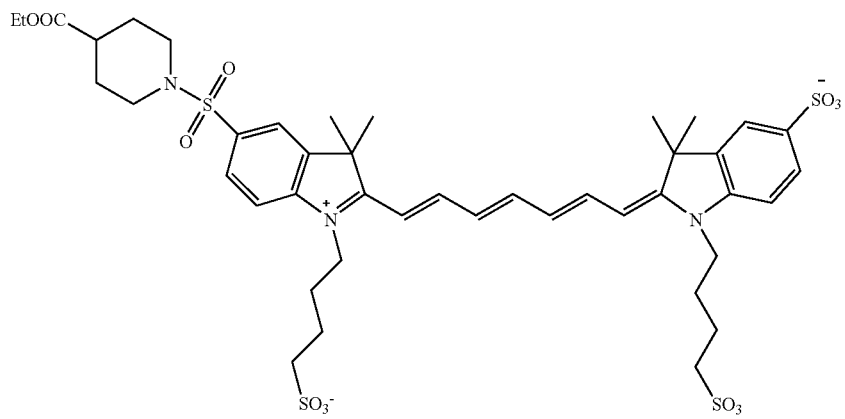

0.1 g of 2,3,3-Trimethyl-1-(3-sulfonatobutyl)-indolinium-5-sulfonate (0.25 mmol) was heated with 0.072 g of N-[5-(Phenylamino)-2,4-pentadienyldene]aniline monohydrochloride (MW 284.8, 0.25 mmol) in 10 mL of acetic anhydride at 110° C. for one hour. The contents were cooled down to 0° C. with stirring. 0.133 g (0.25 mmol) of the quaternary salt XIII was added followed by an addition of 0.082 g of sodium acetate (1 mmol, 4 eq.) After stirring for 10 min at 0° C., the flask was warmed up to room temp over 15 min and then gradually heated to 65° C. over 30 min. Heating continued at 65° C. for 7 hours. Reaction progress was monitored by HPLC, which showed the presence of all the three expected dye products, and the desired asymmetric dye in fairly large amount (about 55%). The reaction mixture was mixed with ether which precipitated the dye along with sodium acetate. The residue was collected by filtration on a sintered funnel (medium pore size), washed well with ether, dried and dissolved in water, which was purified on a preparative RPC18 HPLC column. All fractions corresponding to three dyes were collected, solvent evaporated on speed vac and dried. Each fraction was identified by MALDI. MALDI-TOF-MS m/e 952.18 [M+1]+ calculated for $C_{43}H_{57}N_3O_3S_4^+$, found 952.26 $\lambda_{max}$ (H$_2$O)=758 nm.

The desired asymmetric dye, XIV was obtained in 42% yield, 0.1 g.

Part E. Preparation of Example 2

0.05 g of compound XIV (ethyl ester) was dissolved in 1 mL of water in a 20 mL glass vial and cooled down to 0° C. with stirring. 100 uL of 2M sodium hydroxide solution was added in drops and the stirring continued for 1 hr at 0° C. HPLC showed a complete hydrolysis of ethyl ester to carboxylic acid. The aqueous solution was neutralized with 5M hydrochloric acid (100 uL) and then dried on speed vac. The resulting compound was used in the next step without further purification for activation, which was carried out using disuccinimidyl carbonate and DMAP in DMF at 65° C. for 30 min. $\lambda_{max}$ (H$_2$O)=748 nm.

Example 3

Synthesis of Example 3

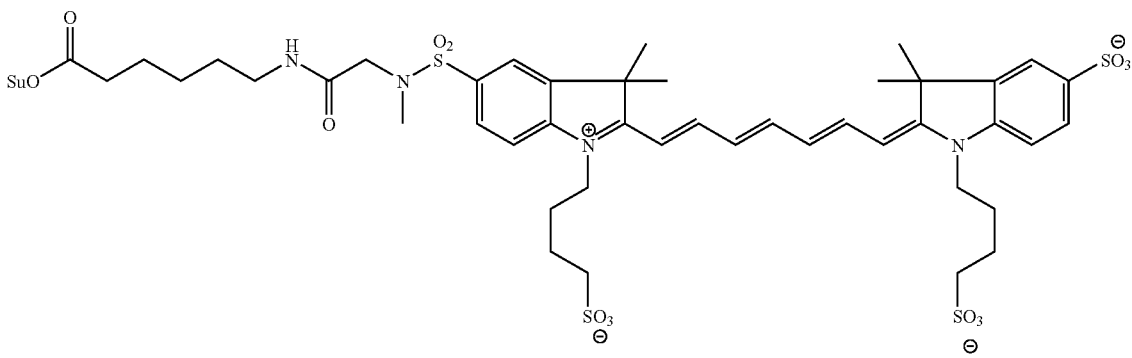

Part A. Preparation of Compound XV

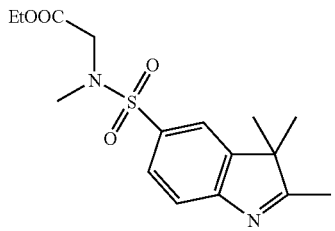

3.0 g of 2,3,3-trimethyl indolinine 5-sulfonyl chloride (9.65 mmol) as obtained above was dissolved in 25 mL dry acetonitrile and cooled down to 0° C. 1.86 g of Ethyl(N-methyl) glycinate (12.11 mmol), dissolved in 5 mL acetonitrile and 3 mL triethylamine was added in drops over 2 min. Dark brown solution turned yellow first and then orange. After 3 hrs stirring at 0° C., reaction mixture was allowed to warm up to room temp. Completion of the reaction was revealed by TLC (silica gel, 19% acetonitrile in dichloromethane and 1% triethylamine). Solvents were removed by rotovap. Concentrated crude material was chromatographed over silica gel and eluted using acetonitrile-methylene chloride mixture, (10% to 50% gradient). A yield of 1.7 g of yellow material was obtained, at 50%. IR (1732 cm$^{-1}$ for ester)

Part B. Preparation of Compound XVI

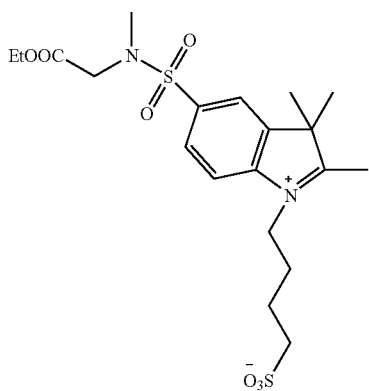

The sulfonamide XV, 1.7 g (5 mmol) from above was reacted with 2 mL of 1,4-butane sultone (20 mmol) in 20 mL of 1,2-dichlorobenzene and heated at 125° C. for an overnight (16 h). Precipitation of the viscous solution with ether, and washings with a mixture of hexane and acetone afforded 1.5 g of desired quaternary salt as a dark brown powder (yield 63%).

Part C. Preparation of Compound XVII

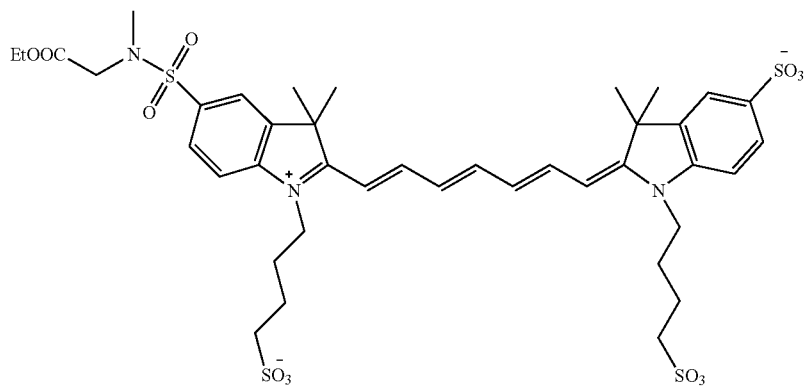

0.22 g of compound XVI (0.55 mmol) was heated with 0.157 g of N-[5-(Phenylamino)-2,4-pentadienyldene]aniline monohydrochloride (0.55 mmol) in 10 mL of acetic anhydride at 110° C. for one and half hour. The contents were cooled down to 0° C. with stirring and 0.261 g (0.55 mmol) of the quaternary salt potassium, 1-(6-sulfonatobutyl)-2,3,3-trimethylindolenine-5-sulfonate was added followed by an addition of 0.1 g of sodium acetate (1.22 mmol, 2.2 eq.) After stirring for 20 min at 0° C., the flask was warmed up to room temp over 15 min and then gradually heated to 70° C. over 45 min. Heating continued at 70° C. for 4 hours. Progress of the reaction was followed by HPLC, which showed all the three expected dye products with the desired asymmetric dye in fairly larger amount (about 50%). The reaction mixture was mixed with ether which precipitated the dye along with sodium acetate. The residue was collected by filtration on a sintered funnel (medium pore size), washed well with ether, and the organic solvents dried. The crude dye was dissolved in water, filtered through a 0.2 uM filter and then purified on a preparative RPC18 HPLC column, solvent evaporated on speed vac and dried to give XVII (43%). MALDI-TOF-MS m/e 912.12 [M+1]+ calculated for $C_{40}H_{53}N_3O_{13}S_4^+$, found 912.22.

Part D. Preparation of Compound XVIII

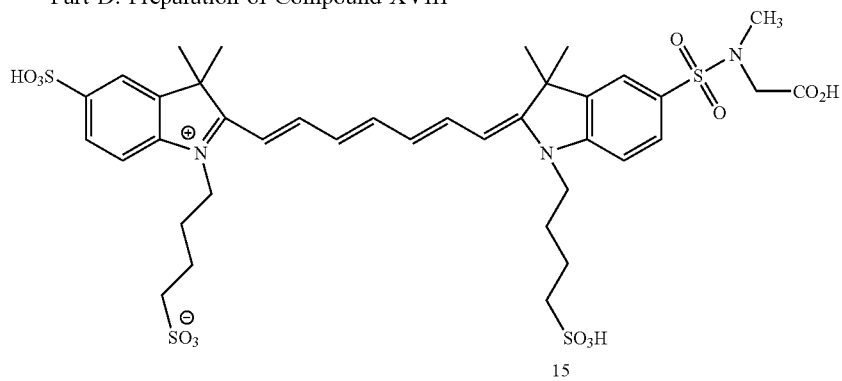

0.22 g of compound XVII was dissolved in 10 mL of water in a round bottom flask and cooled down to 0° C. with stirring. 0.5 mL of 2M sodium hydroxide solution was added in drops and the stirring continued for 1 hr at 0° C. HPLC showed a >98% completion of the hydrolysis of ethyl ester to carboxylic acid. The aqueous solution was neutralized with 5M hydrochloric acid (0.25 mL) and then dried on speed vac. The resulting compound was used in the next step without further purification for activation. The identity was confirmed by mass spec analysis. (yield 0.19 g, 90%)

Part E. Preparation of compound XIX

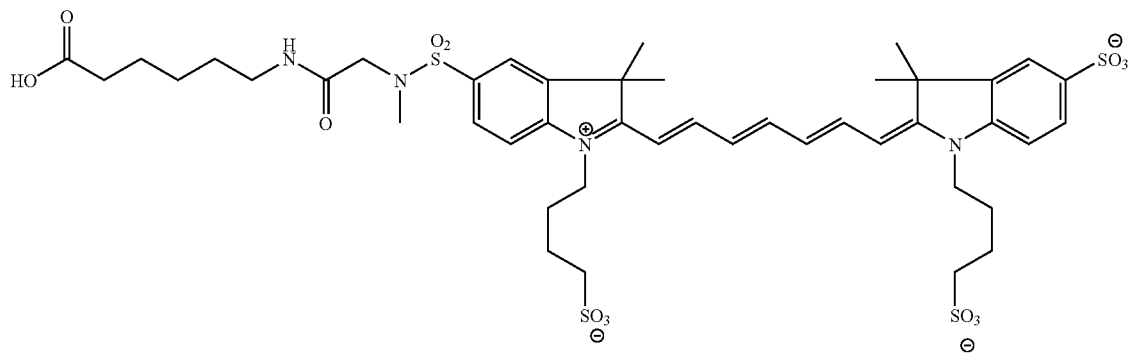

150 mg of XVIII (0.160 mmol) was reacted with 206 mg of DCC (1 mmol) and 138 mg of N-hydroxysuccinimide (1.2 mmol) in 1 mL dry DMF at room temp for 16 hrs. The precipitate of dicyclohexylurea was centrifuged and the intermediate in DMF was collected. MALDI-TOF-MS m/e 1025.10 [M]+ calculated for $C_{42}H_{50}N_4Na_2O_{15}S_4^+$, found 1025.27.

The intermediate was then added to an aqueous solution of 6-aminocaproic acid (210 mg, 1.6 mmol, in 2 mL water) cooled to 0° C. with stirring. The progress of the conjugation was monitored by RP HPLC. The aqueous DMF solution was concentrated by rotovap and then purified by preparatory HPLC to give compound XIX.

The purified product was characterized by mass spec analysis. (yield 110 mg, 69%)

Part F. Preparation of Example 3

Compound XIX was activated by heating a solution of the dye in dry DMF with DSC and DMAP at 65° C. for 90 min to give the title compound.

Example 4

Synthesis of Example 4

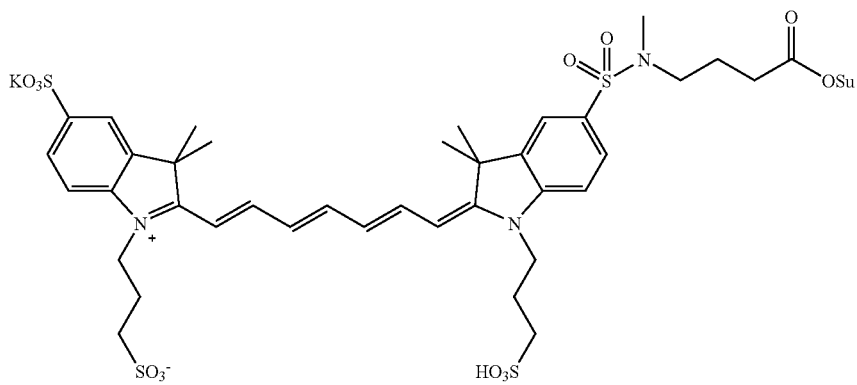

Part A. Preparation of 5-(SO$_2$—NMe-CH$_2$CH$_2$CH$_2$CO$_2$Et)-2,3,3-trimethyl-(3H)-indole (XX)

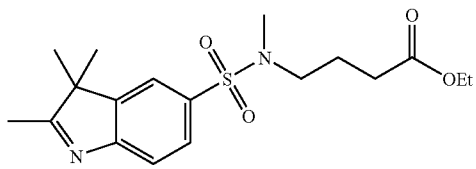 [SMILES: CCOC(=O)CCCN(C)S(=O)(=O)c1ccc2c(c1)C(C)(C)C(C)=N2]

Under a flow of dry nitrogen, 1.2 g sulfonyl chloride XI (4.0 mmol) was added to a dry 100 mL round bottom followed by 25 mL of dry acetonitrile, and the solution was cooled in an ice bath. The hydrochloride salt of N-methyl butyric acid ethyl ester (1.5 g, 8.1 mmol) was dissolved in 25 mL dry acetonitrile and converted to the corresponding free base with the addition of 1.2 mL triethylamine (8.9 mmol). The solution was cooled and, once the quaternary salts settled, was decanted into a pressure equalized addition funnel. The amine was added dropwise at 0° C. with vigorous stirring over the course of 30 minutes. Once the addition was complete, the ice bath was removed, and the reaction was allowed to proceed at room temperature for one hour. The solvent was removed by rotary evaporation under reduced pressure, and purified by column chromatography. A silica column was prepared with 1% triethylamine and 20% acetonitrile in dichloromethane and gradually changed to 30% acetonitrile. 660 mg of the sulfonamide XX (1.7 mmol, 42%) was obtained as an orange oil after evaporation of the eluent. The sulfonamide was subsequently dried overnight in a vacuum dessicator with open potassium hydroxide to ensure the indolenine remained in its free base form.

MALDI-TOF m/z (intensity): 367.0837 (100%).

Part B. Preparation of 1-(γ-Sulfonatopropyl)-5-(SO$_2$—NMe-CH$_2$CH$_2$CH$_2$CO$_2$Et)-2,3,3-trimethyl-(3H)-indole (XXI)

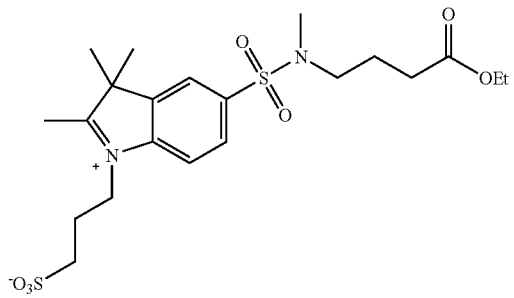

The sulfonamide XX (660 mg, 1.8 nmol) was dissolved in 5 mL 1,2-dichlorobenzene and transferred to a 100 mL pressure tube. After the addition of 157 ul 1,3-propane sultone (1.82 mmol), the reaction vessel was flushed with dry nitrogen, sealed, and placed in 130° C. oil bath. Heating was stopped after 8 hours. The oily purple solids were sonicated with 5 mL acetone followed by 75 mL diethyl ether until the solids settled as a fine powder. The purple solids were filtered and dried under reduced pressure to give XXI.

MALDI-TOF m/z (intensity): 489.1463 (100%).

Part C. Preparation of compound XXII

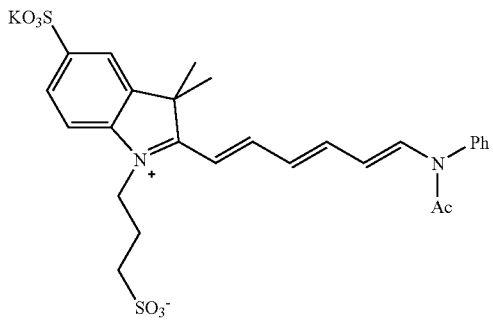

A 100 mL pressure tube was charged with 520 mg of quaternized indolenine (1.3 mmol) and 370 mg N-[5-(phenylamino)-2,4-pentadienylidene]aniline monohydrochloride (1.3 mmol). The reagents dissolved upon the addition of 3 mL acetic acid and 3 mL acetic anhydride with stirring. The tube was flushed with dry nitrogen, sealed, and heated for 3 hours at 110° C. After cooling to room temperature, the product was precipitated with the addition of 50 mL diethyl ether yielding 740 mg.

Part D. Preparation of Ethyl Ester (XXIII)

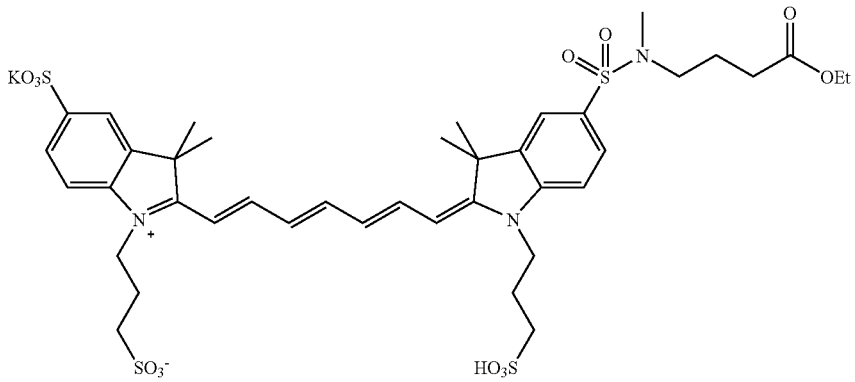

A 2-neck 100 mL round bottom flask was charged with 3 mL acetic acid and 3 mL acetic anhydride, followed by 500 mg of XXI (1.0 mmol). The temperature was maintained at 75° C. and 560 mg of XII (1.0 mmol) was added in four equal portions over two hours. After the first addition, 200 mg sodium acetate (2.4 mmol) was added. After six hours, the dye was precipitated in diethyl ether, filtered, and dried under reduced pressure. HPLC was used to isolate the desired product.

Part E. Preparation of compound XXIV

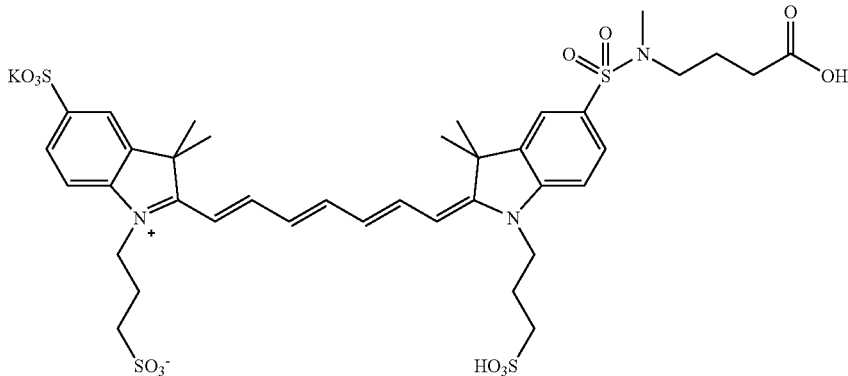

The volume of an aqueous solution of XXIII (125 µmol) was brought to 25 mL with water and cooled in an ice bath. After cooling, 6.2 mL 1N aqueous sodium hydroxide solution was added with vigorous stirring. The ice bath was removed and the reaction proceeded for one hour at room temperature before being stored at 4° C. overnight. The reaction was neutralized to pH 7.0 with 1N hydrochloric acid at 0° C. The solvent was reduced and the reaction desalted on a C18 column. The relatively pure product was repurified by preparative HPLC. After removing the eluent, the product XXIV was dissolved in dry acetonitrile, precipitated in diethyl ether, filtered, and dried in vacuo to yield 179 mg blue solids.

MALDI-TOF m/z (intensity): 884.2034 (100%).

Part F. Preparation of Example 4

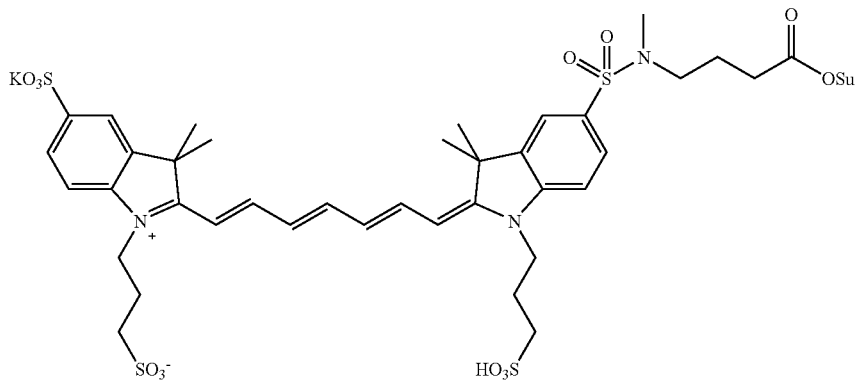

The carboxylic acid XXIV (10.7 mg, 12.2 µmol) was dissolved in 1 mL dry dimethylformamide followed by 4.6 mg disuccinimidylcarbonate (18 µmol) and 2.2 mg dimethylaminopyridine (18 µmol.) The reaction was heated at 60° C. for forty minutes. After cooling to room temperature, the activated ester was precipitated in diethyl ether and recovered on a 0.22 µm filter.

Example 5

Synthesis of Example 5

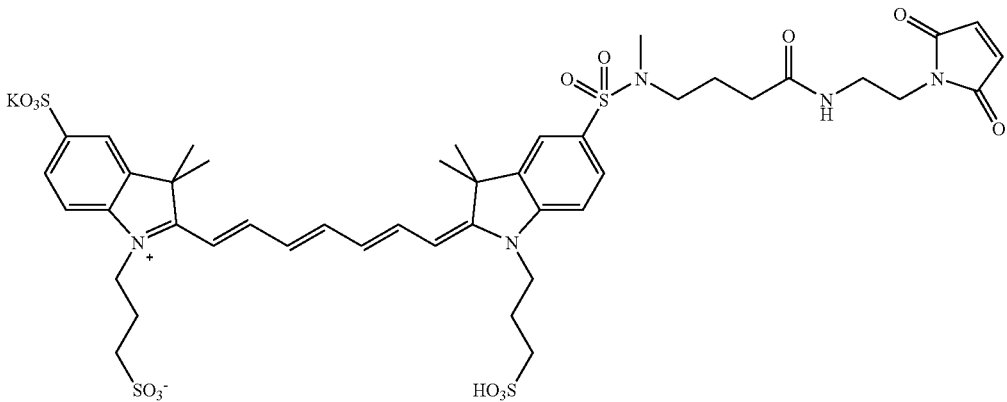

1.4 mg maleimide N-ethylamine trifluoroacetate salt (7.2 µmol) and 3.8 µL diisopropylethylamine (22 µmol) were added sequentially to 1 mL dry dimethylformamide. This solution was added directly to a vial containing 1.0 mg dry succinimide ester (1.0 µmol). The vial was sealed and rotated in the dark at room temperature overnight. HPLC Method A: 8.235 min (750 nm). The desired compound was isolated using preparative HPLC.

MALDI-TOF m/z (intensity): 1006.3552 (55%).

Example 6

Cell Labeling

Mouse splenocytes are prepared as a single cell suspension, and the T cell subpopulation within the splenocyte preparation are enriched by passage over a column that removes B cells and macrophages (R& D kit, Mouse T-cell enrichment columns, MTCC500). T cells are centrifuged to generate a cell pellet of $10^7$ cells. The supernatant is removed from the cell pellet, and a solution of 10 mg/ml Compound A in 100 ul is added. Cells are incubated at room temperature for 5 minutes, followed by 2 rounds of centrifugation and resuspension in physiologic buffer to wash away unbound Compound A. Cells are assessed by fluorescence microscopy.

Example 7

Cell Labeling and In Vivo Imaging

Mouse 4T1 breast adenocarcinoma cells are centrifuged to generate a cell pellet of $10^7$ cells. The supernatant is removed from the cell pellet, and a solution of 10 mg/ml Compound A in 100 uL is added. Cells are incubated at room temperature for 5 minutes, followed by 2 rounds of centrifugation and resuspension in physiologic buffer to wash away unbound Compound A. Cells are assessed by fluorescence microscopy. Cells are injected intravenously into mice at $5 \times 10^5$ cells per mouse, and live mice are imaged by fluorescent molecular tomography immediately after injection and 24 hours after injection. As 4T1 cells primarily metastasize to the lungs, lung fluorescence is quantified.

Example 8

A solution of Compound A was chemically linked to an Arg-Gly-Asp containing peptide under basic conditions to yield a biocompatible fluorescent molecule for in vivo optical imaging. The tumor cell line HT-29 (human colon carcinoma/HTB-38) was obtained from ATCC (Manassas, Va.). HT-29 cells were grown in McCoy's supplemented with 10% FBS at 37° C. in a humidified atmosphere containing 5% $CO_2$. Exponentially growing cells were trypsinized and re-suspended in Hank's Balanced Salt Solution at a concentration of $3 \times 10^7$ cells/ml. Female NU/NU mice 6-8 weeks old (Charles River Laboratory, Wilmington, Mass.) were injected subcutaneously with $3 \times 10^6$ HT-29 cells bilaterally in the first mammary fat pads. One week later, when tumors were approximately 30 $mm^3$, mice were injected intravenously with the fluorescent molecule, (in 150 µl of 1×PBS) and imaged after 24 hrs on a fluorescence reflectance system (FRI, Kodak 2000MM) system and Vis-En's Fluorescence Tomography System (FMT).

Example 9

A solution of Compound A was chemically linked to a bisphosphonate containing biomolecule under basic conditions to yield a biocompatible fluorescent molecule for in vivo optical imaging. Five day-old BALB/c×CF-1 $F_1$ mice were injected subcutaneously with the fluorescent molecule (in 15 µl 1×PBS) and imaged 24 hrs later using a fluorescence reflectance imaging (FRI) system (Kodak 2000MM). Areas of bone growth could be clearly seen.

Example 10

10 mg of the NHSEster of compound X of the present invention is dissolved in 100 uL dry DMF, to which is added a solution of 3-azidopropylamine (5 mg) in 20 uL dry DMSO, and the mixture rotated at room temperature for one hour. 1 mL ether is added to the reaction mixture, and centrifuged for 10 minutes. The supernatant solution is discarded, and the residue is dried on speed vac for 5 minutes, redissolved in water and purified on a RPC18 semi-prep column. The fraction corresponding to the product is collected, and dried on speedvac.

Example 11

10 mg of the NHSEster of compound X of the present invention is dissolved in 100 uL dry DMF, to which is added a solution of 3-propargylamine (5 mg) in 10 uL dry DMSO, and the mixture is rotated at room temperature for one hour. 1 mL ether is added to the reaction mixture, and centrifuged for 10 minutes. The supernatant solution is discarded, and the residue is dried on speed vac for 5 minutes, redissolved in water and purified on a RPC18 semi-prep column. The fraction corresponding to the product is collected, and dried on speedvac.

Example 12

17 mg of the NHSEster of compound X of the present invention is dissolved in 250 uL dry DMF, to which is added a solution of 2-(2-aminoethyl-dithio)pyridine hydrochloride (11 mg) in 10 uL dry DMSO and 4 uL of triethylamine, and the mixture is rotated at room temperature for an overnight. 1 mL ethyl acetate is added to the reaction mixture, and centrifuged for 10 minutes. The supernatant solution is discarded, and the residue is dried on speedvac for 5 minutes, redissolved in water and purified on a RPC18 semi-prep column. The fraction corresponding to the product is collected, and dried on speedvac.

While this invention has been particularly shown and described with references to preferred embodiments thereof, it will be understood by those skilled in the art that various changes in form and details may be made therein without departing from the scope of the invention encompassed by the appended claims.

What is claimed is:

1. A biocompatible fluorescent molecule consisting of a biomolecule covalently linked to a fluorescent compound consisting of the structural formula:

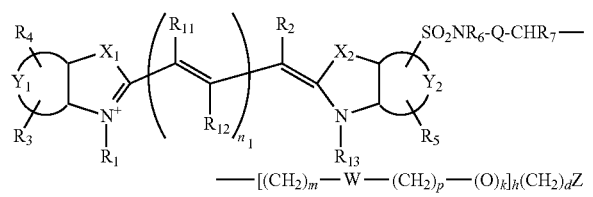

or a salt thereof, wherein:
  $X_1$ and $X_2$ are both $-C(CH_3)_2$;
  $Y_1$ and $Y_2$ are each independently a benzo-condensed ring or a naphtha-condensed ring;
  $n_1$ is 1, 2, or 3;
  $R_2$, $R_{11}$ and $R_{12}$ are independently H, halogen, $C_1$-$C_6$ alkyl, or $C_1$-$C_6$ alkoxy;
  $R_1$ and $R_{13}$ are $(CH_2)_xCH_3$, wherein x is an integer selected from 0 to 6; or $R_1$ and $R_{13}$ are independently $(CH_2)_nSO_3^-$ or $(CH_2)_nSO_3H$ wherein n is an integer selected from 2 to 6;
  $R_3$, $R_4$ and $R_5$ are independently selected from the group consisting of H, carboxylate, carboxylic acid, carboxylic ester, amine, amide, sulfonamide, hydroxyl, alkoxyl, a sulphonic acid moiety and a sulphonate moiety;
  $R_6$ is $C_1$-$C_{10}$ alkyl;
  Q is unsubstituted $C_1$-$C_6$ alkyl group;
  $R_7$ is H, unsubstituted $C_1$-$C_{20}$ aliphatic, unsubstituted aryl, or unsubstituted alkylaryl, wherein $R_7$ is optionally substituted with halogen; or
  $NR_6$, Q, and $CHR_7$ together form

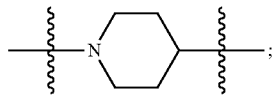 [SMILES: *C1CCN(*)CC1]

h=0; k=0; d=0; m=0; p=0; and
  Z is selected from the group consisting of a carboxylic acid, a succinimidyl ester of a carboxylic acid, a substituted N-hydroxysuccinimido ester, and a maleimide;
  wherein the biomolecule is selected from the group consisting of an amino acid, peptide, protein, glycoprotein, bisphosphonate, and a cell, and
  wherein the biomolecule becomes covalently linked to the fluorescent compound via a reaction with Z to produce the biocompatible fluorescent molecule.

2. The biocompatible fluorescent molecule of claim 1 wherein the fluorescent compound has absorption and emission maxima between 400 nm and 900 nm.

3. The biocompatible fluorescent molecule of claim 2, wherein the compound has absorption and emission maxima between 600 and 800 nm.

4. The biocompatible fluorescent molecule of claim 1, wherein the biomolecule is a labeled cell.

5. The biocompatible fluorescent molecule of claim 1, wherein the moiety $-SO_2NR_6$-Q-$CHR_7-$ is $-SO_2N(CH_3)-CH_2CH_2CH_2-$.

6. The biocompatible fluorescent molecule of claim 1, wherein the moiety $-SO_2NR_6$-Q-$CHR_7-$ is of formula:

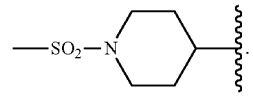

7. The biocompatible fluorescent molecule of claim 1, wherein $R_6$ is $CH_3$.

8. The biocompatible fluorescent molecule of claim 1, wherein the group $-((C(R_{11})=C(R_{12}))_{n1}-C(R_2)=$ is represented by a structural formula selected from the group consisting of:

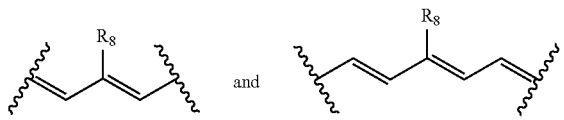

wherein $R_8$ is selected from the group consisting of H or Cl, Br or F.

9. A composition comprising a biocompatible fluorescent molecule as claimed in claim 1 and a physiologically relevant carrier.

10. A method of in vivo optical imaging, the method comprising:
  (a) administering to a subject one or more biocompatible fluorescent molecules of claim 1;
  (b) allowing time for the biocompatible fluorescent molecule to distribute within the subject or to contact or interact with a biological target;

(c) illuminating the subject with light of a wavelength absorbable by the biocompatible fluorescent molecule; and (d) detecting the optical signal emitted by the biocompatible fluorescent molecule.

11. The method of claim 10, wherein the signal emitted by the biocompatible fluorescent molecule is used to construct an image.

12. The method of claim 10, wherein steps (a)-(d) are repeated at predetermined intervals thereby allowing for evaluation of the emitted signals of the biocompatible fluorescent molecule in the subject over time.

13. The method of claim 10, wherein the subject is an animal or human.

14. The method of 10, wherein in step (a) two or more biocompatible fluorescent molecules whose signal properties are distinguishable are administered to a subject.

15. The method of claim 10, wherein the illuminating and detecting steps are performed using an endoscope, catheter, tomographic system, hand-held optical imaging system, surgical goggles, or intraoperative microscope.

* * * * *

UNITED STATES PATENT AND TRADEMARK OFFICE
CERTIFICATE OF CORRECTION

| | |
|---|---|
| PATENT NO. | : 9,574,085 B2 |
| APPLICATION NO. | : 12/065387 |
| DATED | : February 21, 2017 |
| INVENTOR(S) | : Narasimhachari Narayanan et al. |

It is certified that error appears in the above-identified patent and that said Letters Patent is hereby corrected as shown below:

In the Claims

In Claim 8, at Column 66, Line 56-57, delete "H or Cl, Br, or F" and replace it with --H, Cl, Br and F--.

Signed and Sealed this
Twenty-second Day of May, 2018

Andrei Iancu
*Director of the United States Patent and Trademark Office*